US010548655B2

(12) United States Patent
Scheib et al.

(10) Patent No.: US 10,548,655 B2
(45) Date of Patent: Feb. 4, 2020

(54) CONTROL AND ELECTRICAL CONNECTIONS FOR ELECTRODE ENDOCUTTER DEVICE

(71) Applicant: Ethicon Endo-Surgery, LLC, Guaynabo, PR (US)

(72) Inventors: Charles J. Scheib, Loveland, OH (US); Mark S. Zeiner, Mason, OH (US); David C. Yates, West Chester, OH (US)

(73) Assignee: Ethicon LLC, Guaynabo, PR (US)

( * ) Notice: Subject to any disclaimer, the term of this patent is extended or adjusted under 35 U.S.C. 154(b) by 598 days.

(21) Appl. No.: 14/885,348

(22) Filed: Oct. 16, 2015

(65) Prior Publication Data

US 2017/0105782 A1    Apr. 20, 2017

(51) Int. Cl.
*A61B 18/12* (2006.01)
*A61B 18/14* (2006.01)
(Continued)

(52) U.S. Cl.
CPC ...... *A61B 18/1206* (2013.01); *A61B 18/1445* (2013.01); *A61B 17/068* (2013.01);
(Continued)

(58) Field of Classification Search
CPC ........... A61B 2017/00017; A61B 2017/00123; A61B 2017/00398; A61B 2017/07228; A61B 2017/07257; A61B 2017/07271; A61B 17/068; A61B 17/07207; A61B 18/1206; A61B 18/1442; A61B 18/1445;
(Continued)

(56) References Cited

U.S. PATENT DOCUMENTS

| D278,081 S | 3/1985 | Green |
| D297,764 S | 9/1988 | Hunt et al. |

(Continued)

FOREIGN PATENT DOCUMENTS

| CA | 2576440 A1 | 7/2007 |
| EP | 2243439 A1 | 10/2010 |

(Continued)

OTHER PUBLICATIONS

Bay Area Circuits (https://bayareacircuits.com/multi-layer-stackups/) (Year: 2015).

*Primary Examiner* — Daniel W Fowler

(57) ABSTRACT

Aspects of the present disclosure include an attachable power and control system to supply energy to electrodes of a wiping electrode coagulation system of a surgical device. A surgical device includes electrodes at an end of effector to aide in sealing during various surgical procedures. During the procedure, the surgeon may wipe the surgical site with the end effector, causing the electrodes to touch the fractured area. Electrosurgical energy may be applied to the electrodes during the wiping, causing coagulation of smaller vessels. The attachable power and control system may be configured to slide over the shaft of the surgical device. The power and control system also may be configured to supply power to the electrodes and to control when energy is applied to the electrodes, based in part, for example, on measuring a distance or angle of the opening of the jaws at the end effector.

12 Claims, 30 Drawing Sheets

(51) Int. Cl.
  *A61B 17/068* (2006.01)
  *A61B 18/00* (2006.01)
(52) U.S. Cl.
  CPC ............ *A61B 2018/00178* (2013.01); *A61B 2018/00184* (2013.01); *A61B 2018/00404* (2013.01); *A61B 2018/00529* (2013.01); *A61B 2018/00589* (2013.01); *A61B 2018/00642* (2013.01); *A61B 2018/00702* (2013.01); *A61B 2018/00988* (2013.01); *A61B 2018/1452* (2013.01); *A61B 2018/1495* (2013.01)
(58) Field of Classification Search
  CPC ........... A61B 2018/00589; A61B 2018/00601; A61B 2018/00607; A61B 2018/0063; A61B 2018/00642; A61B 2018/00708; A61B 2018/00773; A61B 2018/00779; A61B 2018/1452
  See application file for complete search history.

(56) References Cited

U.S. PATENT DOCUMENTS

| | | | |
|---|---|---|---|
| 5,007,907 A | 4/1991 | Nishigaki et al. | |
| 5,364,395 A * | 11/1994 | West, Jr. | A61B 17/32002 604/22 |
| 5,403,312 A | 4/1995 | Yates et al. | |
| D360,688 S | 7/1995 | Ferragamo et al. | |
| 5,485,947 A | 1/1996 | Olson et al. | |
| 5,658,281 A * | 8/1997 | Heard | A61B 18/1445 606/41 |
| 5,735,848 A * | 4/1998 | Yates | A61B 17/07207 227/175.1 |
| 5,817,093 A | 10/1998 | Williamson, IV et al. | |
| 6,004,320 A * | 12/1999 | Casscells | A61B 17/32002 606/170 |
| D480,808 S | 10/2003 | Wells et al. | |
| 6,730,081 B1 * | 5/2004 | Desai | A61B 17/00234 604/8 |
| D509,297 S | 9/2005 | Wells | |
| 7,223,267 B2 | 5/2007 | Isola et al. | |
| 7,383,611 B2 | 6/2008 | Foster | |
| D576,278 S | 9/2008 | Nalagatla et al. | |
| 7,617,961 B2 | 11/2009 | Viola | |
| D605,762 S | 12/2009 | Nalagatla et al. | |
| 7,780,663 B2 | 8/2010 | Yates et al. | |
| 7,819,296 B2 | 10/2010 | Hueil et al. | |
| 7,861,906 B2 | 1/2011 | Doll et al. | |
| D650,074 S | 12/2011 | Hunt et al. | |
| 8,485,413 B2 | 7/2013 | Scheib et al. | |
| 8,517,239 B2 | 8/2013 | Scheib et al. | |
| 8,579,176 B2 | 11/2013 | Smith et al. | |
| 8,608,045 B2 | 12/2013 | Smith et al. | |
| 8,622,274 B2 | 1/2014 | Yates et al. | |
| 8,746,533 B2 | 6/2014 | Whitman et al. | |
| 8,764,747 B2 | 7/2014 | Cummings et al. | |
| 8,840,603 B2 | 9/2014 | Shelton, IV et al. | |
| 8,888,771 B2 | 11/2014 | Twomey | |
| 9,060,775 B2 | 6/2015 | Wiener et al. | |
| 9,072,535 B2 | 7/2015 | Shelton, IV et al. | |
| 9,149,325 B2 | 10/2015 | Worrell et al. | |
| 9,326,788 B2 | 5/2016 | Batross et al. | |
| 9,510,906 B2 | 12/2016 | Boudreaux et al. | |
| 9,572,622 B2 | 2/2017 | Shelton, IV et al. | |
| 9,629,627 B2 | 4/2017 | Kostrzewski et al. | |
| 9,706,993 B2 | 7/2017 | Hessler et al. | |
| 9,724,095 B2 | 8/2017 | Gupta et al. | |
| 9,743,929 B2 | 8/2017 | Leimbach et al. | |
| D800,904 S | 10/2017 | Leimbach et al. | |
| 9,788,836 B2 | 10/2017 | Overmyer et al. | |
| 9,795,379 B2 | 10/2017 | Leimbach et al. | |
| 9,814,514 B2 * | 11/2017 | Shelton, IV | A61B 18/1447 |
| 9,839,421 B2 | 12/2017 | Zerkle et al. | |
| 9,844,375 B2 | 12/2017 | Overmyer et al. | |
| 9,877,722 B2 | 1/2018 | Schellin et al. | |
| D809,659 S | 2/2018 | Menn | |
| 9,913,642 B2 | 3/2018 | Leimbach et al. | |
| 9,924,998 B2 | 3/2018 | Martin et al. | |
| 9,968,355 B2 | 5/2018 | Shelton, IV et al. | |
| 9,980,769 B2 | 5/2018 | Trees et al. | |
| 10,010,366 B2 | 7/2018 | Strobl | |
| D831,209 S | 10/2018 | Huitema et al. | |
| 10,178,992 B2 | 1/2019 | Wise et al. | |
| 10,194,912 B2 | 2/2019 | Scheib et al. | |
| 10,201,348 B2 | 2/2019 | Scheib et al. | |
| 10,213,198 B2 | 2/2019 | Aronhalt et al. | |
| 10,245,027 B2 | 4/2019 | Shelton, IV et al. | |
| 2002/0147447 A1 * | 10/2002 | Long | A61B 18/1492 606/41 |
| 2004/0122423 A1 | 6/2004 | Dycus et al. | |
| 2005/0261677 A1 * | 11/2005 | Hall | A61B 18/1442 606/48 |
| 2006/0064086 A1 | 3/2006 | Odom | |
| 2009/0206133 A1 | 8/2009 | Morgan et al. | |
| 2010/0193566 A1 | 8/2010 | Scheib et al. | |
| 2011/0028964 A1 * | 2/2011 | Edwards | A61B 18/1442 606/33 |
| 2012/0059371 A1 * | 3/2012 | Anderson | A61B 18/1445 606/45 |
| 2012/0245576 A1 | 9/2012 | Epstein et al. | |
| 2013/0138096 A1 * | 5/2013 | Benn | A61B 18/1206 606/33 |
| 2014/0263541 A1 | 9/2014 | Leimbach et al. | |
| 2014/0263552 A1 | 9/2014 | Hall et al. | |
| 2015/0060519 A1 | 3/2015 | Shelton, IV et al. | |
| 2015/0196347 A1 | 7/2015 | Yates et al. | |
| 2015/0297235 A1 | 10/2015 | Harris et al. | |
| 2015/0297236 A1 | 10/2015 | Harris et al. | |
| 2016/0270842 A1 | 9/2016 | Strobl et al. | |
| 2017/0105786 A1 | 4/2017 | Scheib et al. | |
| 2017/0119388 A1 | 5/2017 | Kostrzewski | |
| 2017/0143336 A1 | 5/2017 | Shah et al. | |
| 2017/0312019 A1 | 11/2017 | Trees et al. | |
| 2018/0168621 A1 | 6/2018 | Shelton, IV et al. | |
| 2018/0168650 A1 | 6/2018 | Shelton, IV et al. | |
| 2018/0360452 A1 | 12/2018 | Shelton, IV et al. | |
| 2019/0000463 A1 | 1/2019 | Shelton, IV et al. | |
| 2019/0000464 A1 | 1/2019 | Shelton, IV et al. | |
| 2019/0000468 A1 | 1/2019 | Adams et al. | |
| 2019/0000472 A1 | 1/2019 | Shelton, IV et al. | |
| 2019/0000478 A1 | 1/2019 | Messerly et al. | |
| 2019/0000479 A1 | 1/2019 | Harris et al. | |
| 2019/0000525 A1 | 1/2019 | Messerly et al. | |
| 2019/0000531 A1 | 1/2019 | Messerly et al. | |
| 2019/0000532 A1 | 1/2019 | Shelton, IV et al. | |
| 2019/0000533 A1 | 1/2019 | Messerly et al. | |
| 2019/0000534 A1 | 1/2019 | Messerly et al. | |
| 2019/0000535 A1 | 1/2019 | Messerly et al. | |
| 2019/0000536 A1 | 1/2019 | Yates et al. | |
| 2019/0000537 A1 | 1/2019 | Widenhouse et al. | |
| 2019/0000538 A1 | 1/2019 | Widenhouse et al. | |
| 2019/0000539 A1 | 1/2019 | Messerly et al. | |

FOREIGN PATENT DOCUMENTS

| | | |
|---|---|---|
| EP | 2764832 A2 | 8/2014 |
| EP | 3009082 A1 | 4/2016 |
| EP | 3015080 A2 | 5/2016 |
| WO | WO-9937225 A1 | 7/1999 |

\* cited by examiner

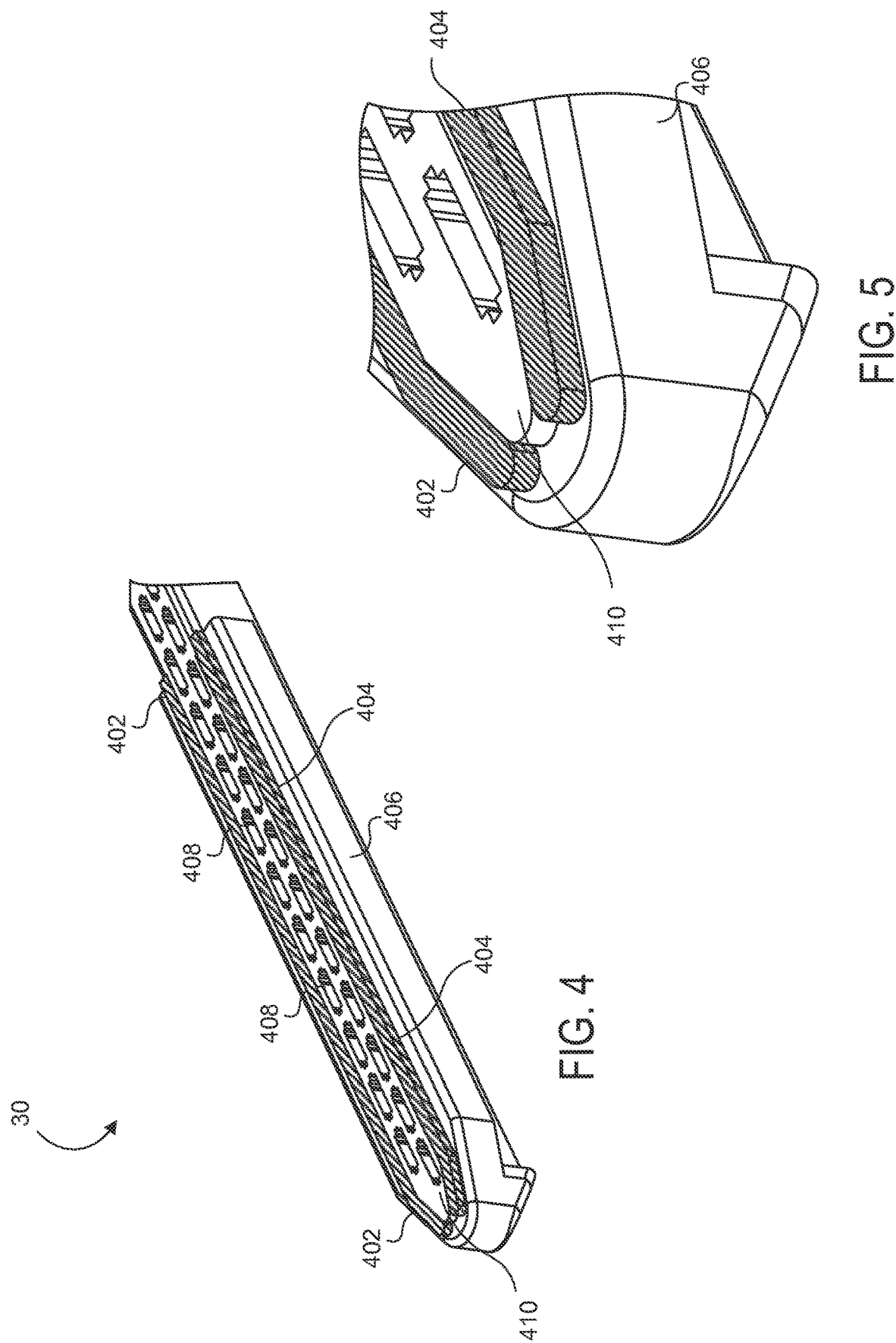

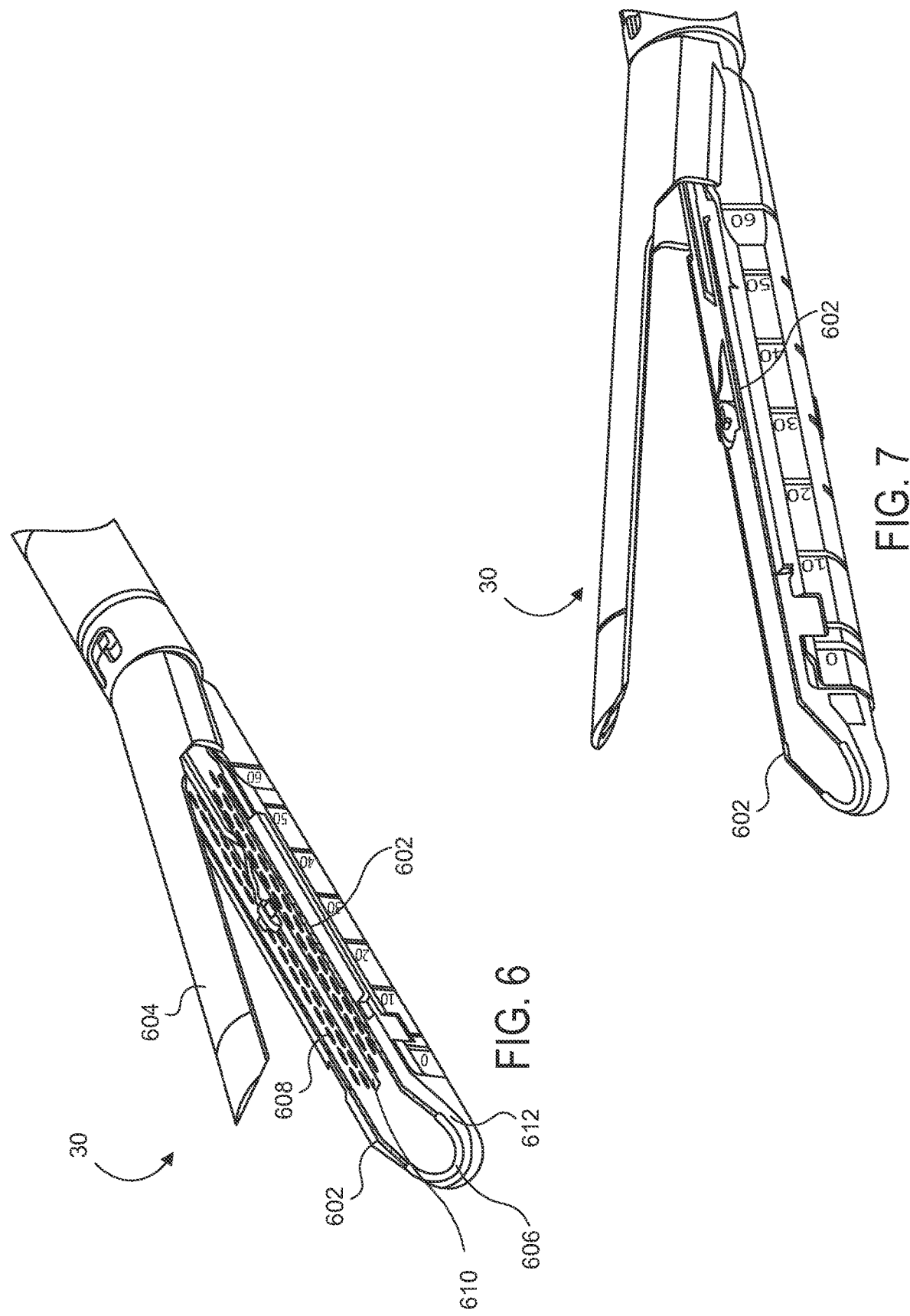

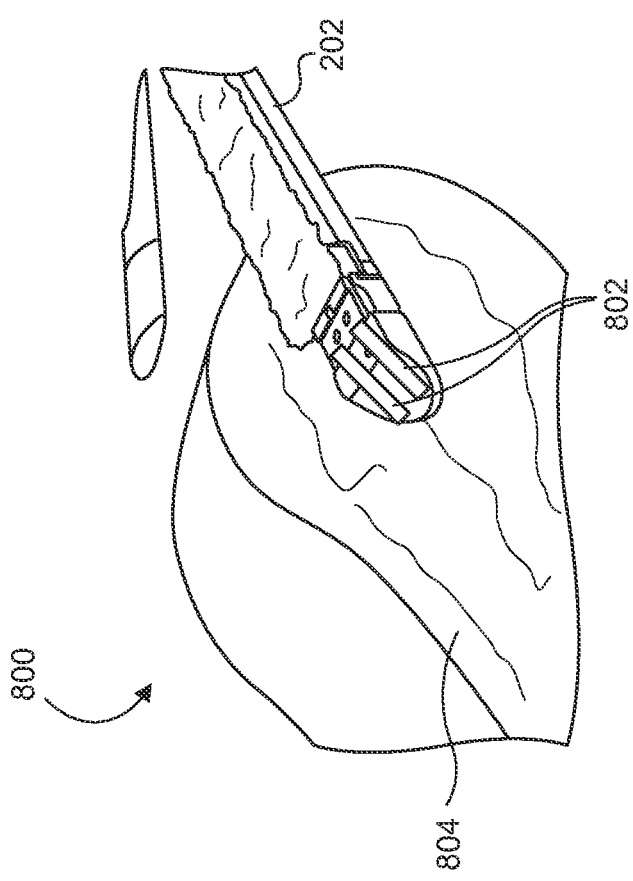
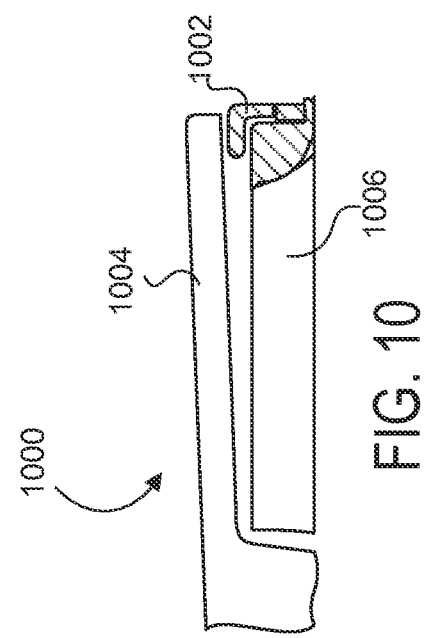

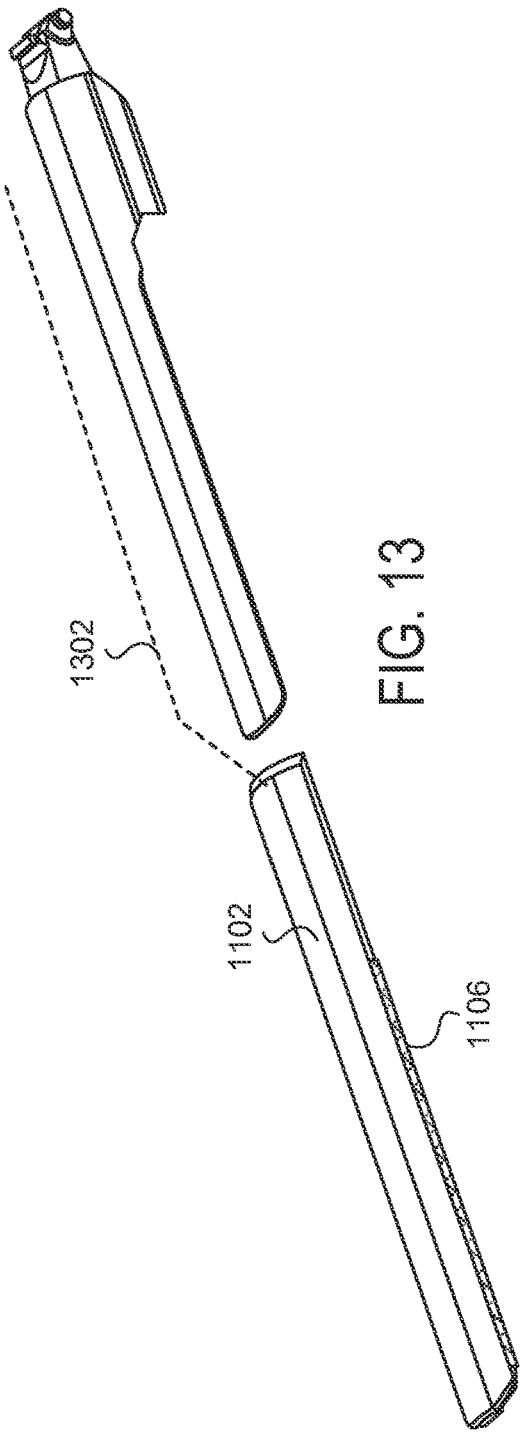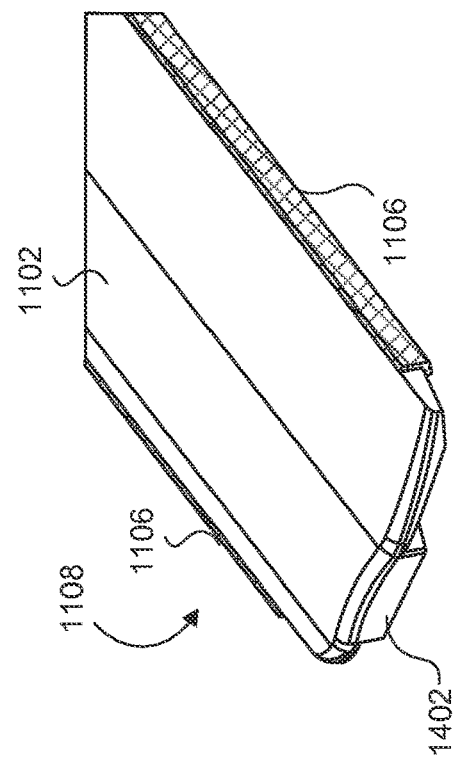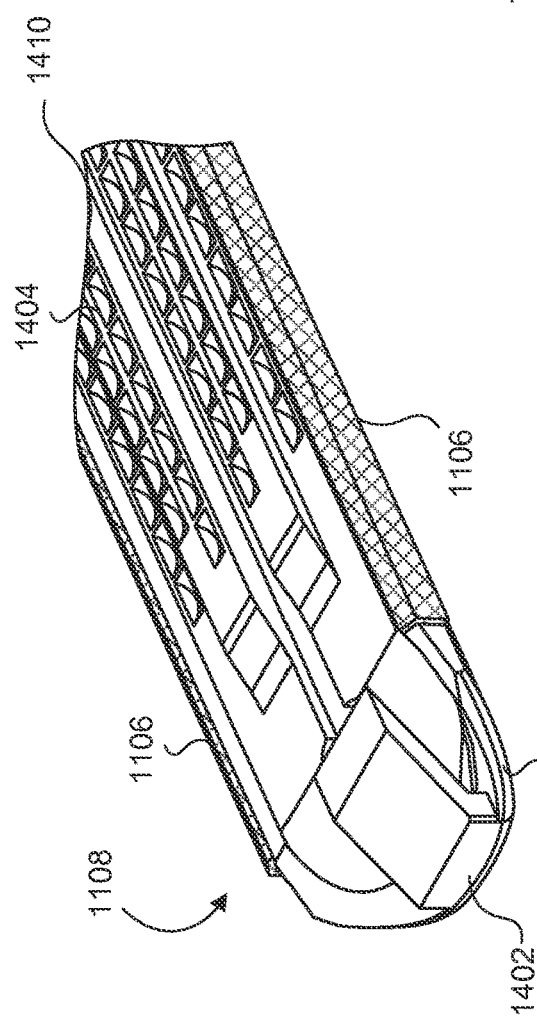

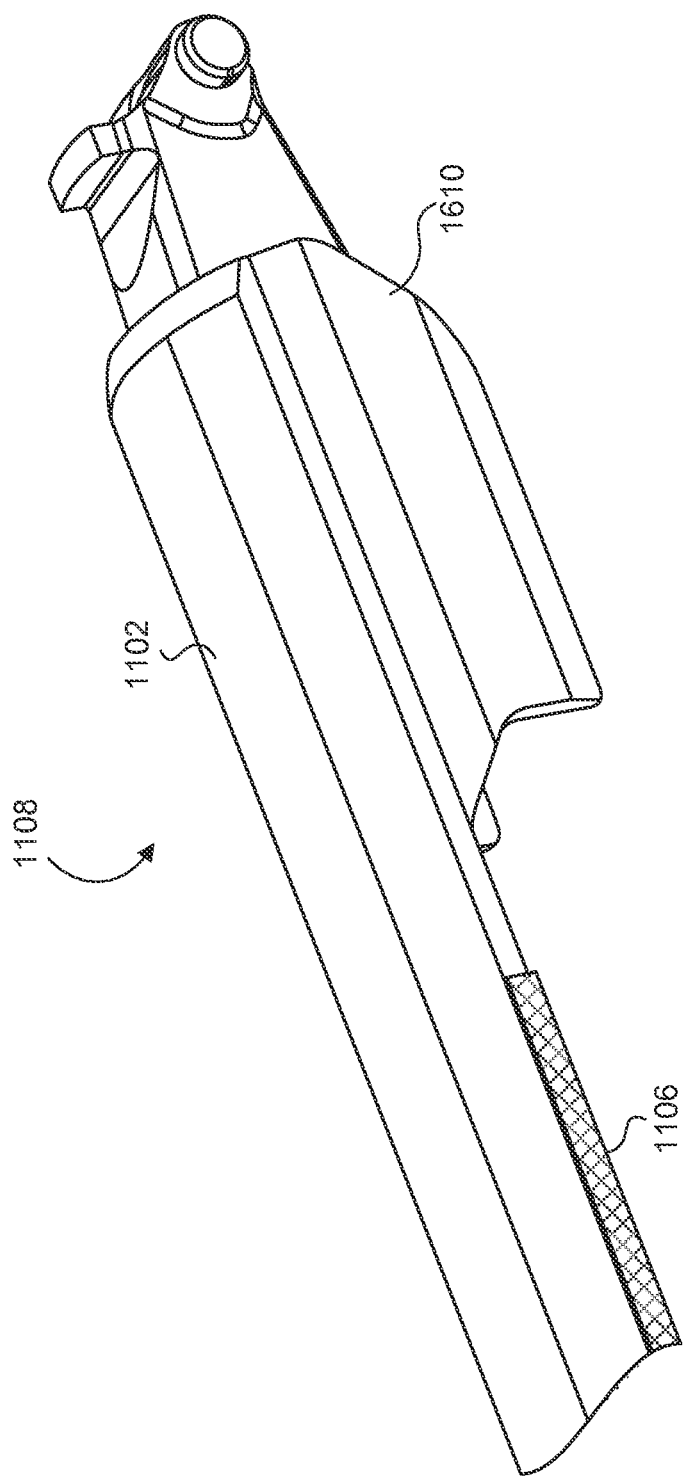

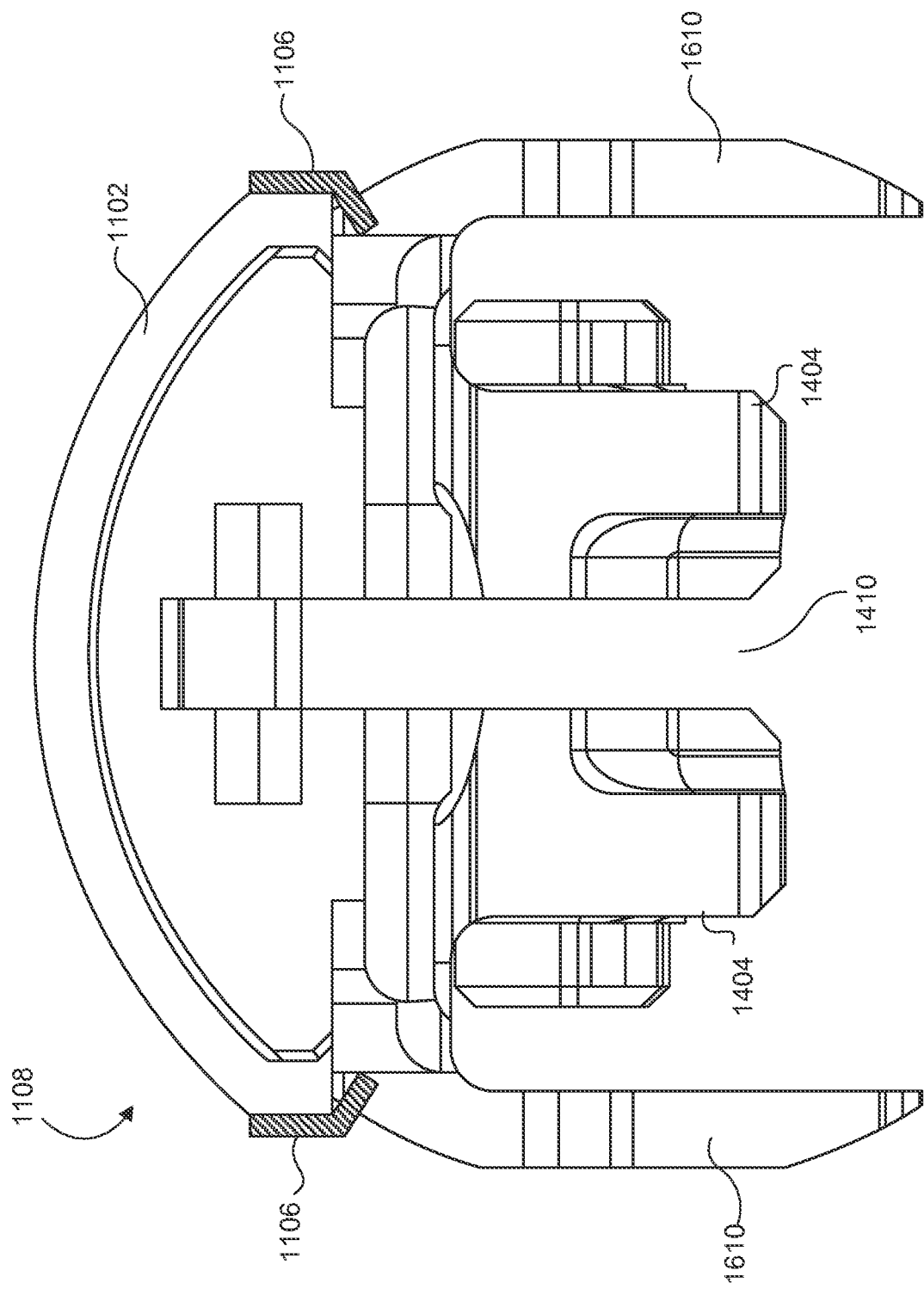

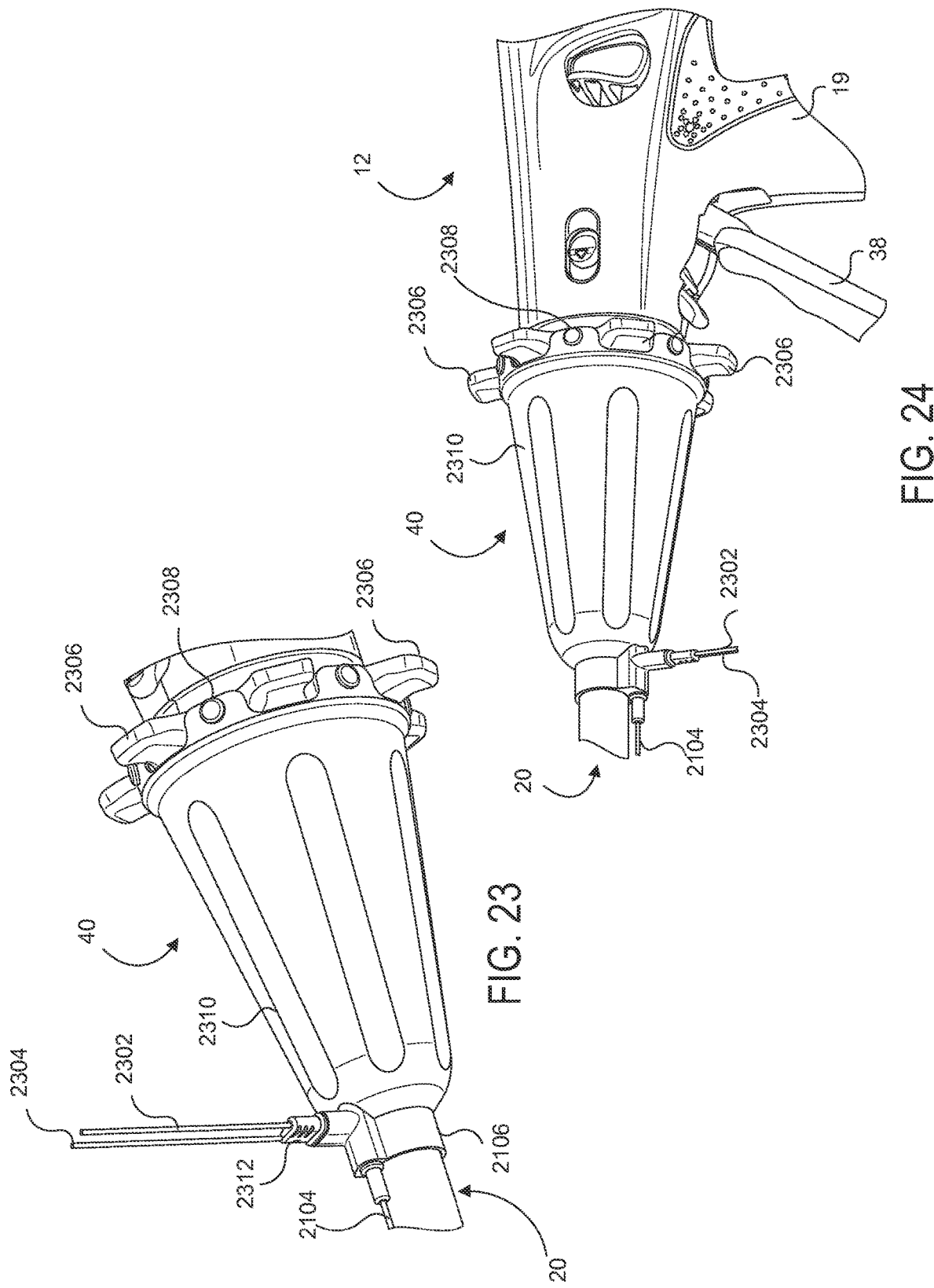

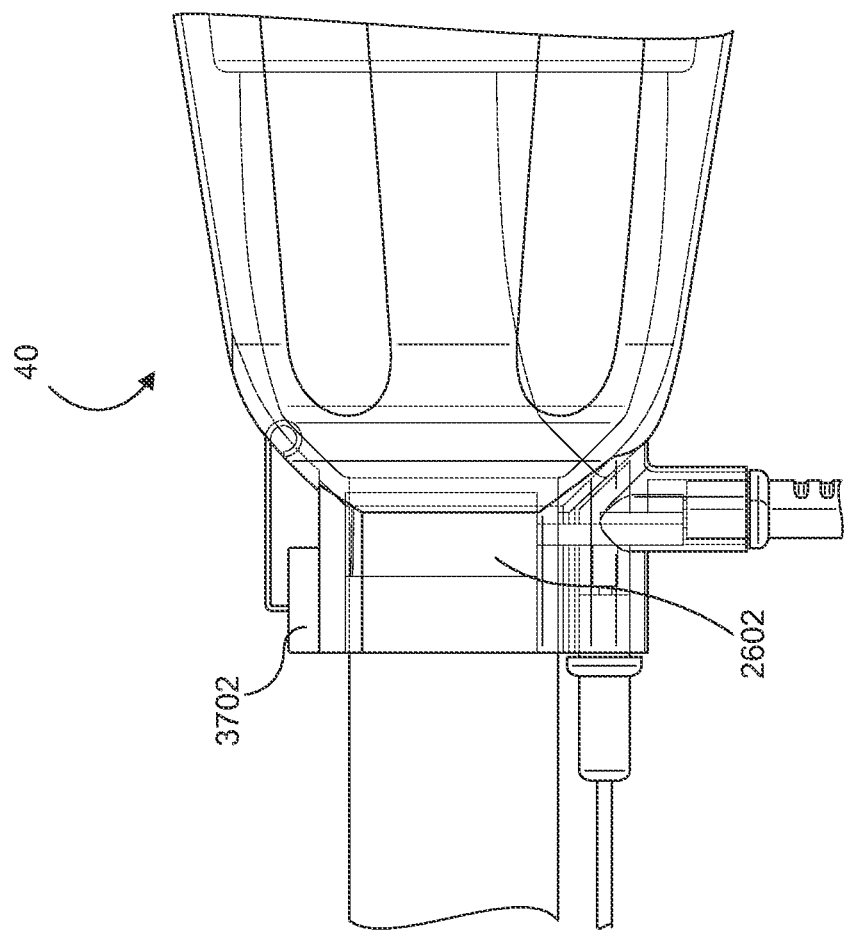

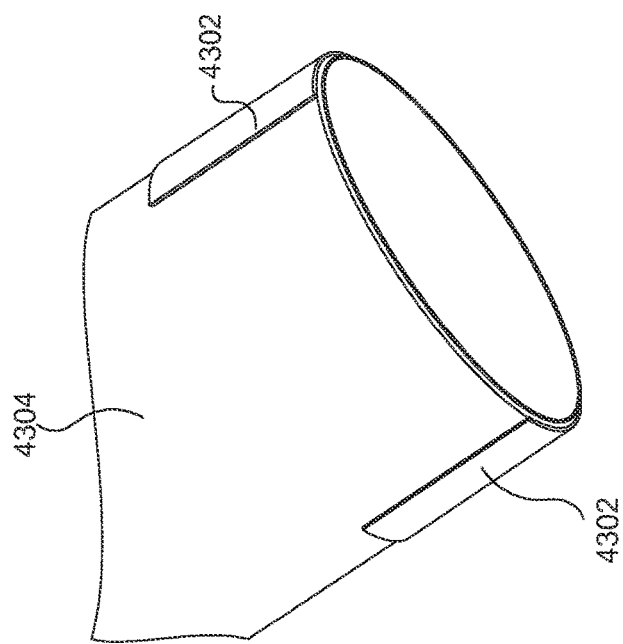
FIG. 47
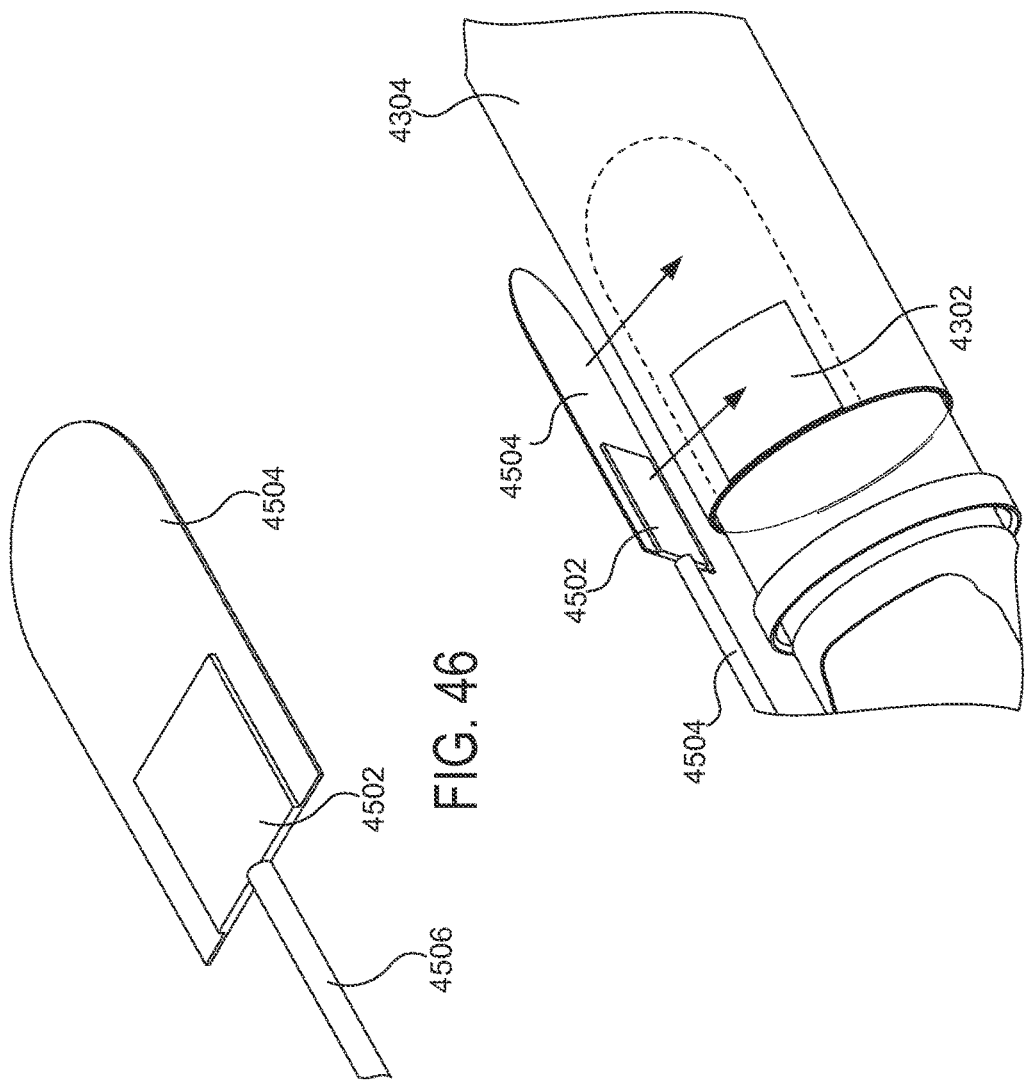
FIG. 46
FIG. 48

CONTROL AND ELECTRICAL CONNECTIONS FOR ELECTRODE ENDOCUTTER DEVICE

CROSS REFERENCE TO RELATED APPLICATION

This application is related to U.S. non-provisional application Ser. No. 14/885,341, filed concurrently herewith, and titled "ELECTRODE WIPING SURGICAL DEVICE," the entire disclosure of which is hereby incorporated by reference in its entirety and for all purposes.

TECHNICAL FIELD

The present disclosure is related generally to medical devices with various mechanisms for cutting and sealing tissue. In particular, the present disclosure is related to power and control apparatuses for medical devices with stapling and cutting instruments having electrodes positioned at the end effector for sealing in a wiping motion, suitably for performing surgical procedures on the liver.

BACKGROUND

When performing certain surgical procedures, there is a challenge to control bleeding and provide sealing of smaller vessels of tissue at the surgical site. For example, in a liver resection, also referred to as a hepatectomy, there is a challenge to create a resection plane through several inches of liver parenchyma. Within this parenchyma are bile ducts, arteries portal veins (bringing blood in) and hepatic veins (allowing blood out). When parenchyma is separated, there is a challenge to prevent bleeding, seal small (1-2 mm) bile ducts as well as larger 9+ mm vessels. There is also a challenge to isolate critical ducts and vessels without damaging them.

While several devices have been made and used, it is believed that no one prior to the inventors has made or used the device described in the appended claims.

BRIEF SUMMARY

In some embodiments, a power and control assembly for a wiping electrode coagulation system of a surgical device is provided.

1. In one example, the power and control assembly comprises: a housing structure configured to be attached to the surgical device around a shaft of the surgical device, the housing structure comprising a first wire and a second wire both coupled to a power source, the first wire further electrically coupled to a metal component of the surgical device, the second wire further electrically coupled to the wiping electrode coagulation system positioned at an end effector at a distal end of the surgical device; wherein the housing structure is further configured to be detachable from shaft of the surgical device; and wherein the power and control assembly is configured to provide power to the wiping electrode coagulation system.

2. In another example of the power and control assembly, the housing structure is configured to be rotatable around the shaft as the shaft rotates the end effector.

3. In another example of the power and control assembly, the housing structure further comprises a rotatable knob.

4. In another example of the power and control assembly, the power and control assembly comprises a plurality of buttons spacedly distributed around the rotatable knob, wherein each of the plurality of buttons is configured to enable power to the wiping electrode coagulation system when activated.

5. In another example of the power and control assembly, the housing structure further comprises a molded slidable electrical contact electrically coupled to the shaft of the surgical device and configured to slide in line with the shaft as the shaft translates along a longitudinal axis.

6. In another example of the power and control assembly, the electrical contact is electrically coupled to the first wire and is further configured to providing electrical grounding of the power and control assembly.

7. In another example, the power and control assembly further comprises at least one button configured to enable power to the wiping electrode coagulation system when activated.

8. In another example of the power and control assembly, the at least one button is electrically coupled to a control loop feedback system configured to enable power to the wiping electrode coagulation system based on a distance of a position of a first jaw of the surgical device in relation to a position of a second jaw of the surgical device.

9. In another example of the power and control assembly, the control loop feedback system comprises a tumbler electrically coupled to the at least one button and mechanically coupled to the shaft, the tumbler configured to slide as the shaft translates along a longitudinal axis.

10. In another example of the power and control assembly, the control loop feedback system is further configured to enable power to the wiping electrode coagulation system based on a measured distance the tumbler slides within the slot relative to a distal end of the housing structure.

11. In another example of the power and control assembly, the control loop feedback system is further configured to enable power to the wiping electrode coagulation system when the tumbler slides a maximal distance relative to the distal end of the housing structure and to disable power to the wiping electrode coagulation system when the tumbler slides a minimal distance relative to the distal end of the housing structure.

12. In another example of the power and control assembly, the control loop feedback system is further configured to enable a degree of power to the wiping electrode coagulation system in proportion to the distance the tumbler slides within the slot relative to the distal end of the housing structure.

13. In another example, the power and control assembly further comprises a clamp disposed external to the housing structure and configured to be opened in a first position to allow the housing structure to slide along the shaft and configured to be closed in a second position to stably affix the housing structure to the shaft.

14. In another example of the power and control assembly: the housing structure further comprises a molded slidable electrical contact electrically coupled to the shaft of the surgical device and configured to slide in line with the shaft as the shaft translates along a longitudinal axis, the electrical contact is configured to not touch the shaft when the clamp is opened in the first position, and the electrical contact is configured to touch the shaft when the clamp is closed in the second position.

15. In another example, the power and control assembly further comprises an external shaft coupled to the housing structure and configured to slidably attach around the shaft of the surgical device.

16. In another example of the power and control assembly, the external shaft comprises an electrical conductive pad at a distal end of the external shaft that is configured to electrically couple to the wiping electrode coagulation system.

17. In some embodiments, a surgical device is presented. The surgical device may comprise: a handle assembly; a shaft coupled to the handle assembly; an end effector coupled to a distal end of the shaft; a wiping electrode coagulation system coupled to the end effector and comprising at least one electrode, the coagulation system configured to cause coagulation of tissue through application of electrosurgical energy of the at least one electrode when the at least one electrode is wiped against tissue at a surgical site; and a power and control assembly comprising: a housing structure configured to be attached around the shaft, the housing structure comprising a first wire and a second wire both coupled to a power source, the first wire further electrically coupled to the shaft, the second wire further electrically coupled to the wiping electrode coagulation system; wherein the housing structure is further configured to be detachable from shaft; and wherein the power and control assembly is configured to provide power to the wiping electrode coagulation system.

18. In another example of the surgical device, the wiping electrode coagulation system is configured to be detachable from the end effector.

19. In another example of the surgical device, the wiping electrode coagulation system further comprises an electrical connector configured to electrically couple to and decouple from the second wire of the power and control assembly.

20. In some embodiments, a non-transitory computer readable medium is presented. The computer readable medium may comprise instructions that, when executed by a processor of a machine, cause the processor to perform operations comprising: measuring a distance from between a first jaw of an end effector of a surgical instrument and a second jaw of the end effector of the surgical instrument and controlling a level of energy to a wiping electrode coagulation system positioned at the end effector based on the measured distance.

21. In another example of the computer readable medium, the operation further comprise: determining that the first jaw and the second jaw form a closed position based on the measured distance and enabling power to the wiping electrode coagulation system based on determination of the closed position.

22. In some embodiments, a method for sealing tissue is presented. The method may include any of the procedures described in examples 1-21.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The novel features of the embodiments described herein are set forth with particularity in the appended claims. The embodiments, however, both as to organization and methods of operation may be better understood by reference to the following description, taken in conjunction with the accompanying drawings as follows:

FIG. 4 shows another example placement for electrodes, in this case, having two separate strips of electrodes placed longitudinally on the sides of the stapling surface, according to some embodiments.

FIG. 5 shows a close-up view of the distal end of the jaw having the two electrodes, according to some embodiments.

FIGS. 6 and 7 show another example implementation for the end effector containing an electrically isolated electrode, in this case showing the electrode placed on the outer edge of the top surface of the jaw, according to some embodiments.

FIG. 8 shows yet another example implementation of electrodes positioned on the end effector of a surgical instrument, in this case, showing two short strips of electrodes positioned at the distal end of the end effector, on the bottom jaw, according to some embodiments.

FIG. 9 shows another variation of the cauterizing or coagulating tip, this time with the electrodes oriented at a 90° offset compared to the positions of the electrodes in FIG. 8, according to some embodiments.

FIG. 10 shows yet another example implementation for placement of one or more electrodes on the end effector, according to some embodiments.

FIG. 13 illustrates an example of where a wire may exit the sleeve to be attached to a power generator for powering the electrode.

FIG. 14 shows the pocket side of the anvil with the attachable sleeve coupled to the opposite top side of the anvil jaw.

FIG. 15 shows a close-up view of the top side of the anvil with the sleeve attached.

FIG. 16 provides another close-up view of the proximal end of the anvil.

FIG. 17 shows a head-on perspective view of the anvil having the attachable sleeve.

FIG. 23 shows a perspective view of the nozzle rotated 180° along the longitudinal axis of the shaft.

FIG. 24 provides another perspective view of the nozzle in context with the surrounding shaft and handle assembly.

FIGS. 36-38 provide illustrations of an alternative design for varying the power applied to the electrodes, in this case, including a sensor placed along a measuring or sliding strip.

FIGS. 43-48 illustrate another alternative design to electrically connecting the electrodes at the end effector to the power and control assembly, in this case including a shaft portion and a nozzle portion both configured to slide over the original shaft of the surgical instrument and including a conductive pad at the distal end of the shaft.

DETAILED DESCRIPTION

Figure 1:
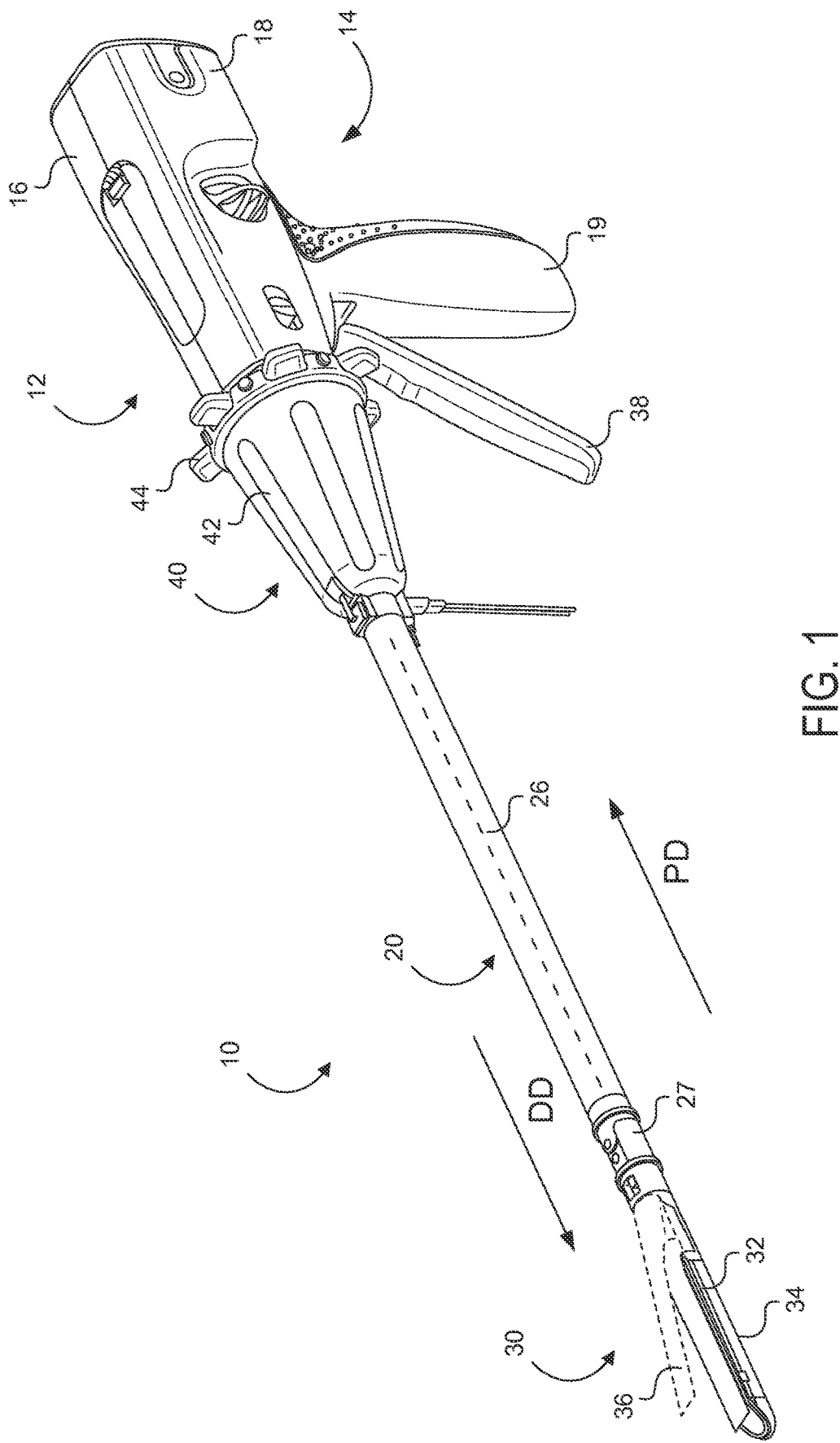
FIG. 1 shows a motor-driven surgical cutting and fastening instrument that may or may not be reused, according to some embodiments.

In the following detailed description, reference is made to the accompanying drawings, which form a part hereof. In the drawings, similar symbols and reference characters typically identify similar components throughout the several views, unless context dictates otherwise. The illustrative embodiments described in the detailed description, drawings, and claims are not meant to be limiting. Other embodiments may be utilized, and other changes may be made, without departing from the scope of the subject matter presented here.

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc., described herein may be combined with any one or more of the other teachings, expressions, embodiments, examples, etc., that are described herein. The following-described teachings, expressions, embodiments, examples, etc., should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Also, in the following description, it is to be understood that terms such as front, back, inside, outside, top, bottom, and the like are words of convenience and are not to be construed as limiting terms. Terminology used herein is not meant to be limiting insofar as devices described herein, or portions thereof, may be attached or utilized in other orientations. The various embodiments will be described in more detail with reference to the drawings. Throughout this disclosure, the term "proximal" is used to describe the side of a component, e.g., a shaft, a handle assembly, etc., closer to a user operating the surgical instrument, e.g., a surgeon, and the term "distal" is used to describe the side of the component further from the user operating the surgical instrument.

Aspects of the present disclosure are presented for a surgical instrument configured for cutting and sealing tissue using a blade and a surgical stapler system coupled with electrodes positioned on the sides for sealing small blood vessels and other ducts. A common use of the surgical instrument presented herein includes performing a hepatectomy, often referred to as a liver resection. A liver resection generally involves the surgical removal of all or a portion of the liver. A liver resection may be needed for removing tumors (benign or malignant) or other diseased portions of a liver, as well as for removing part of a liver for liver transplant.

A surgical instrument with a long, narrow end effector, sometimes including a blade or other cutting instrument, conventionally is used to perform the resection procedure. The end effector may include a pair of jaws to clamp down on the intended area of the liver to be divided, and may include a cutting element in between the jaws to resection the liver. The surgical instrument often may include a fastening (e.g., stapling) element, such that larger vessels and other ducts in the parenchyma of the liver may be sealed with the aide of the fastening element, for example, by clasping tissue between the two jaws of the surgical instrument and stapling the tissue together. However, there is a challenge to control sealing and prevent bleeding from other smaller vessels present in the parenchyma. Conventionally, a second device may be used by the surgeon that applies electrosurgical energy (e.g., radio frequency ("RF") energy) to the surgical site in a careful wiping motion that causes coagulation of the smaller vessels. However, it would be more efficient and safer if the surgeon did not need to switch between multiple devices to complete sealing of the resected liver. The space to operate on is quite narrow for most of the procedure, and it therefore may be inconvenient and even dangerous to continually switch between multiple devices.

Aspects of the present disclosure include a surgical device comprising electrodes on the sides of the end of effector to aide in sealing during a surgical procedure such as a liver resection. During a sealing procedure, the surgeon may wipe the surgical site with the end effector, causing the electrodes to touch the fractured area. Electrosurgical energy may be applied to the electrodes during the wiping, causing coagulation of smaller vessels, such as tiny blood vessels and bile ducts in the parenchyma of the liver. Also, due to the sponge-like and "friable" consistency of the liver tissue, electrosurgical energy should be delicately applied to cause sealing but to avoid overly damaging the liver. In some embodiments, the thin design of the electrodes allows for an appropriate amount of electrosurgical energy to be applied to the fractured area of the liver to seal bile ducts and small vessels.

In some embodiments, an attachable sleeve including the electrodes on the sides is presented that can be fitted onto existing surgical staplers. That is, conventional surgical devices used to perform the cutting portion of the liver resection may essentially be retrofitted with an attachable sleeve to provide the additional functionality of sealing the smaller vessels.

In some embodiments, the surgical device includes a replaceable staple cartridge that supplies the staples and also includes the electrodes on the sides. In this way, conventional surgical devices used to perform the cutting portion and the sealing of larger vessels also may be essentially retrofitted to provide the additional functionality of sealing the smaller vessels when utilizing a cartridge according to aspects of the present disclosure.

In some embodiments, an attachable power and control system to supply energy to the electrodes is presented. The attachable power and control system may be configured to slide over the shaft of the surgical device, or in other cases clamp onto the surgical device. The power and control system also may be configured to supply power to the electrodes and to control when energy is applied to the electrodes, based in part, for example, on measuring a distance or angle of the opening of the jaws at the end effector. For example, the control system may be configured to supply RF energy only when it is determined that the jaws are closed or substantially in a closed position.

Referring to FIG. 1, depicted is a motor-driven surgical cutting and fastening instrument 10 that may or may not be reused. In the illustrated example, the instrument 10 includes a housing 12 that comprises a handle assembly 14 that is configured to be grasped, manipulated, and actuated by the user, such as a surgeon. The housing 12 is configured to operate an end effector 30 configured to perform one or more surgical tasks or procedures through components in a shaft 20 operably coupled thereto. While examples of a user as described herein may include a human user such as a surgeon, it will be understood that the various unique and novel arrangements of the various forms of the surgical device disclosed herein also may be effectively employed in connection with robotically-controlled surgical systems. Thus, the term "housing" also may encompass a housing or similar portion of a robotic system that houses or otherwise operably supports at least one drive system that is configured to generate and apply at least one control motion which could be used to actuate the end effector assemblies disclosed herein and their respective equivalents. The term "frame" may refer to a portion of a handheld surgical instrument. The term "frame" also may represent a portion of a robotically controlled surgical instrument and/or a portion of the robotic system that may be used to operably control a surgical instrument. For example, the interchangeable shaft assemblies disclosed herein may be employed with various robotic systems, instruments, components, and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. US 2012/0298719. U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. US 2012/0298719, is incorporated by reference herein in its entirety.

The housing 12 depicted in FIG. 1 is shown in connection with a shaft assembly 20 that includes an end effector 30 that comprises a surgical cutting and fastening device that is configured to operably support a surgical staple cartridge 34 therein. The end effector 30 includes electrodes (not shown) coupled to the sides or at least on the periphery of the end effector 30 structure that are configured to supply electrosurgical energy to a surgical site to coagulate and seal tissue. An attachable or integrated power and control assembly 40 is also shown that is configured to supply power to the electrodes and to control activation of the electrodes. Further details of the electrodes and the power and control assembly 40 will be shown in the following figures. Furthermore, the end effectors, shaft assemblies, handles, surgical instruments, and/or surgical instrument systems described herein can utilize any suitable fastener, or fasteners, to fasten tissue. For instance, a fastener cartridge comprising a plurality of fasteners removably stored therein can be removably inserted into and/or attached to the end effector of a shaft assembly.

Still referring to FIG. 1, the handle assembly 14 may comprise a pair of interconnectable handle housing segments 16 and 18 that may be interconnected by screws, snap features, adhesive, etc. In the illustrated arrangement, the handle housing segments 16, 18 cooperate to form a pistol grip portion 19 that can be gripped and manipulated by the clinician. The handle assembly 14 may operably support a plurality of drive systems therein that are configured to generate and apply various control motions to corresponding portions of the shaft and end effector.

Regarding the end effector 30 in FIG. 1, the surgical end effector 30 may comprise an elongated channel 32 that is configured to operably support the staple cartridge 34 therein. The end effector 30 may further include an anvil 36 that is pivotally supported relative to the elongated channel 32. The shaft assembly 20 may further include an articulation joint 27 and an articulation lock which can be configured to releasably hold the end effector 30 in a desired position relative to an axis parallel to the shaft assembly 20. Examples of details regarding the construction and operation of the end effector 30, the articulation joint 27 and the articulation lock are set forth in U.S. patent application Ser. No. 13/803,086, filed Mar. 14, 2013, titled ARTICULATABLE SURGICAL INSTRUMENT COMPRISING AN ARTICULATION LOCK, now U.S. Patent Application Publication No. 2014/0263541, the entire disclosure of which is hereby incorporated by reference herein. As shown in later figures, the shaft assembly 20 can further include a proximal attachable housing or nozzle 40 comprised of nozzle portions 42 and 44. The shaft assembly 20 can further include a closure tube 260 which can be utilized to close and/or open the anvil 36 of the end effector 30.

In use, a closure tube 26 is translated in the distal direction ("DD") to close the anvil 36, for example, in response to the actuation of the closure trigger 38. The anvil 36 is closed by distally translating the closure tube 26, causing it to strike a proximal surface on the anvil 36, for example, in the manner described in the aforementioned reference U.S. patent application Ser. No. 13/803,086, now U.S. Patent Application Publication No. 2014/0263541. As was also described in detail in that reference, the anvil 36 is opened by proximally translating the closure tube 26 and a shaft closure sleeve assembly (not shown) in the proximal direction ("PD"), causing a tab and a horseshoe aperture to contact and push against the anvil tab to lift the anvil 36. In the anvil-open position, the shaft closure tube 26 is moved to its proximal position.

Examples of Wiping Electrodes

Figure 2:
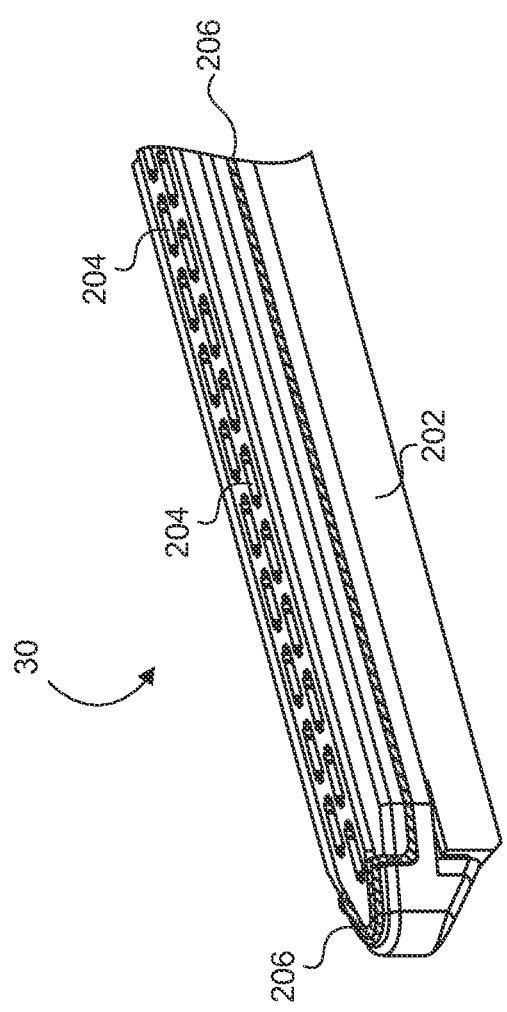
FIG. 2 shows an end effector with a side wiping electrode positioned along the periphery of one of the jaws of the end effector, according to some embodiments.

Referring to FIG. 2, an end effector 30 is shown with a side wiping electrode 206 positioned along the periphery of one of the jaws of the end effector 30, according to some embodiments. As previously described, there is a challenge to effectively seal smaller vessels and other parenchymal wall tissue in certain procedures, such as in a liver resection. The electrodes on the side may be configured to supply electrosurgical energy to a parenchymal wall to coagulate and therefore cause sealing of the smaller vessels.

Still referring to FIG. 2, the electrode 206 is shown as a thin strip running along the lateral side of one of the jaws 202 of the end effector 30. The electrode 206 is also shown to run vertically up the distal end of the jaw 202, and then run horizontally along the distal end of the stapling surface, in this case forming a V shape to match the contour of the distal end. Not shown, the electrode 206 may continue in a symmetrical formation along the opposite lateral side of the jaw 202. The electrode 206 may be affixed to the jaw 202 in various ways, including via glue, clamps, or other fasteners, and molding into the design of the jaw 202 during manufacturing stages. Not shown, the electrode 206 may be powered via a power and control assembly electrically coupled to the electrode 206 by one or more wires.

As shown, the jaw 202 includes the stapler firing mechanism configured to fire the staples through the slots 204. Not shown is the second jaw that would be configured to pivotally close on top of the jaw 202, acting as an anvil to close and fasten the staples to tissue at the surgical site. In some embodiments, the end effector 30 may include a staple firing mechanism affixed to the jaw 202, while in other cases, the staple firing mechanism may be replaceable as a staple cartridge. In some cases, the electrode 206 may be affixed to a permanent structure of the end effector 30. In other cases, the electrode 206 may be a part of a replaceable staple cartridge, embodiments of which are described further below.

Figure 3:
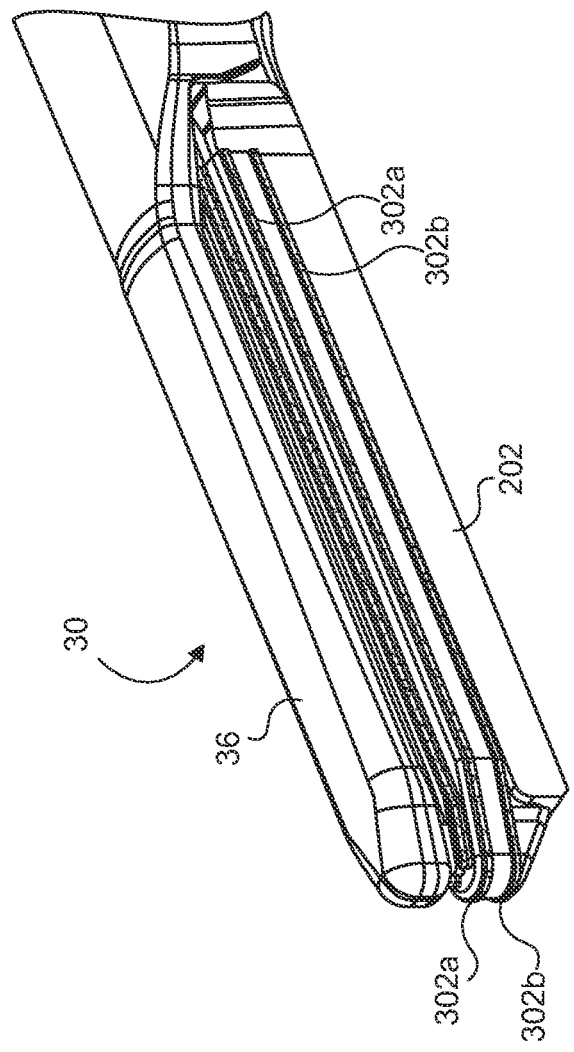
FIG. 3 shows an example of how multiple electrodes may be included at the end effector of the surgical instrument.

Referring to FIG. 3, in some embodiments, multiple electrodes may be included at the end effector 30 of the surgical instrument. Here, electrodes 302a and 302b are shown and positioned to run along the periphery of the bottom jaw 202 in parallel. In this case, both electrodes 302a and 302b run along the outer periphery of the distal end of the end effector 30. In this example design, an anvil 36 can pivotally close on top of the jaw 202 while the electrodes 302a and 302b may still be exposed at the distal end of the end effector 30 to wipe a tissue wall at a surgical site.

Referring to FIG. 4, another example placement for electrodes is shown, according to some embodiments. Here, two separated strips of electrodes 402 and 404 are placed longitudinally on the sides of the stapling surface of the jaw 406. In between the electrodes 402 and 404 is the stapling surface 410 containing one or more rows of firing slots 408 for the staples. Having multiple separated strips of electrodes may allow for multiple options and uses of the electrodes. For example, varying levels of power may be applied to the different electrodes 402 and 404, such that one electrode may be configured to cause coagulation at the surgical site, while another may be more highly powered and configured to cut tissue. Thus, this example allows for one side of the end effector 30 to perform sealing functionality, while the other side may be configured to perform cutting functionality. In some embodiments, the electrodes 402 and 404 may be installed into replaceable staple cartridges such that one set of cartridges may be configured to perform cutting on a first side due to the higher powered electrode on said first side, while a second set of cartridges may be configured to perform the cutting on the opposite side due to the higher part electrode placed on said opposite side.

Referring to FIG. 5, a close-up view of the distal end of the jaw 406 having the two electrodes 402 and 404 is shown. The electrodes 402 and 404 do not touch with one another at the distal end, and are separated by the stapling surface 410. It is noted that in this case, the placement of the electrodes of 402 and 404 being on the top surface of the jaw 406 physically limits exposure of a tissue wall to the electrodes 402 and 404. This may be by design, in that in some embodiments, it is intended for the electrodes to not be fully exposed against the tissue wall to more carefully limit when the electrodes are actually designed to touch the tissue wall. In this case, if at least one of the electrodes 402 or 404 is implemented to perform cutting functionality, then it would be prudent to limit the exposure of said electrode, like shown.

Referring to FIGS. 6 and 7, another example implementation for the end effector 30 containing an electrically isolated electrode is shown. Here, the electrode 602 is placed on the outer edge of the top surface of the jaw 612. A semicircle ring 606 connects the distal ends of two electrodes 602 running longitudinally along multiple rows of staple slots 608. In this example, a cutting element is present in the middle of the staple slots 608, as shown by the available cutting element slot 610. Thus, in some embodiments, the end effector 30 may be configured to perform cutting, fastening, and sealing functionalities all in one. In addition, in this case, the anvil 604 may be configured to interact with the electrode 602 when performing a sealing procedure. For example, power may be supplied to the electrode 602 when the anvil 604 is closed on to the stapling jaw 612, such as when the jaws may be closed on liver parenchyma containing larger vessels that are stapled. While the larger vessels are being stapled, power may be applied to the electrode 602 to seal smaller vessels and ducts around the larger vessels. FIG. 7 shows another perspective view of this example end effector 30.

Referring to FIG. 8, illustration 800 shows yet another example implementation of electrodes positioned on the end effector of a surgical instrument, according to some embodiments. Here, two short strips of electrodes 802 may be positioned at the distal end of the end effector, on the bottom jaw 202. These electrodes 802 may be purposed to act as a cauterizing or coagulating tip of the end effector. In some embodiments, the angled portion of the distal end of the end effector may allow for more accessible reach to coagulate or seal tissue. Illustration 800 presents the example end effector in the context of a surgical site 804. For example, the surgical site 804 may include a portion of the liver in the process of being resected.

Referring to FIG. 9, illustration 900 shows another variation of the cauterizing or coagulating tip, this time with the electrodes 902 oriented at a 90° offset compared to the positions of the electrodes 802.

Referring to FIG. 10, illustration 1000 shows yet another example implementation for placing one or more electrodes, according to some embodiments. A profile view of an end effector includes a stapling jaw 1006 and an anvil jaw 1004, configured to pivotally close on to the bottom jaw 1006. Positioned at the distal end or tip of the bottom jaw 1006 may be placed in electrode 1002, shown here as being bent to run vertically and horizontally along the distal end. This alternative design may allow for some versatility for touching and wiping a tissue wall from various angles. For example, this end effector may be configured to coagulate tissue when the anvil jaw 1004 is closed, due to a portion of the electrode 1002 still being exposed at the tip of the end effector. In addition, tissue that is clamped between the jaws 1004 and 1006 also may be sealed by the electrode 1002.

Based on the examples in FIGS. 2-10, it may be apparent that the placement and designs of the electrode can vary, so long as the electrode may be sufficiently exposed to touch the tissue walls at a surgical site to satisfy varying purposes and functionalities. In addition, it may be apparent that one or more of the example implementations may be combined or modified by any of the other example implementations, and embodiments are not so limited.

Figure 11:
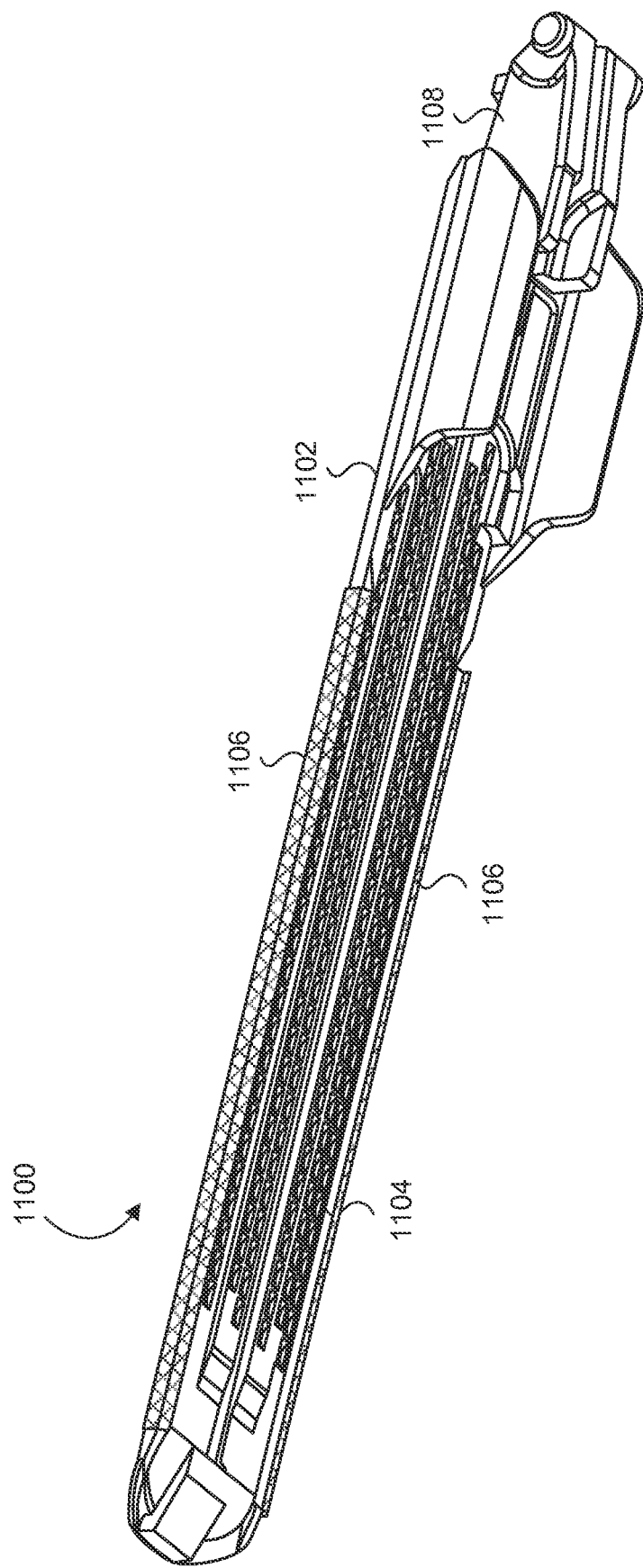
FIG. 11 shows a sleeve coupled with electrodes slidably attached to a top jaw, according to some embodiments.

Referring to FIG. 11, illustration 1100 shows a sleeve 1102 coupled with electrodes 1106 slidably attached to a top jaw 1108, according to some embodiments. The top jaw 1108 may act as the anvil to a stapler mechanism and includes the crimper divots 1104 for closing the staples. The slidable sleeve 1102 including the electrodes 1106 may allow for conventional stapler surgical instruments to be essentially retrofitted with the coagulation swiping functionality afforded by the laterally positioned electrodes 1106. That is, the sleeve 1102 may be formed or molded to attach onto existing anvils of an end effector.

Figure 12:
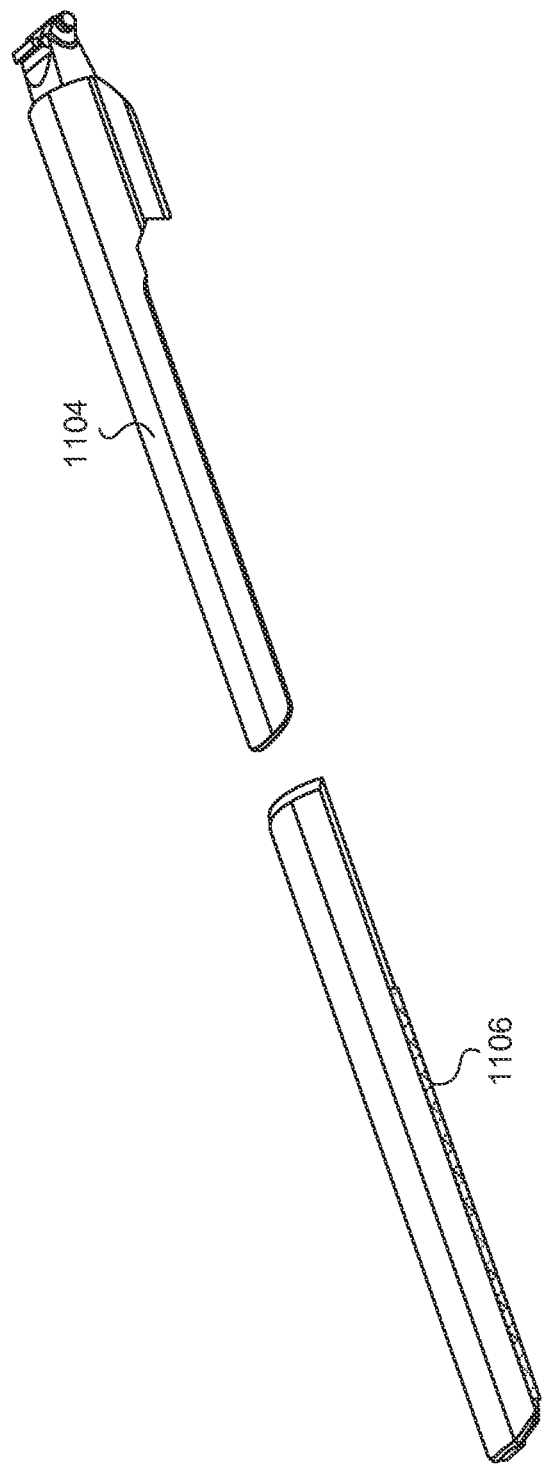
FIG. 12 shows an example of the slidable sleeve separated from a conventional anvil top jaw.

Referring to FIG. 12, shown is an example of the slidable sleeve 1102 separated from the conventional anvil 1104. An electrode 1106 is fixedly attached to the sleeve 1102, which may allow for the end effector to include the wiping functionality that it might not otherwise have. Referring to FIG. 13, a dashed line 1302 illustrates an example of where a wire may exit the sleeve 1102 to be attached to a power generator for powering the electrode 1106. Further discussion on example power generators and control apparatuses will be discussed in later figures.

Referring to FIG. 14, the pocket side of the anvil 1108 is shown. Here, a fastening clamp 1402 is shown to demonstrate how the sleeve 1102 may be coupled to the anvil 1108. It may be apparent from this illustration that the electrodes 1106 are fully exposed on the lateral sides of the anvil 1108, while still allowing for the crimper divots 1404 to be fully accessed by the firing staple mechanism, not shown. In addition, in some embodiments, a cutting slot 1410 may be available in the pocket side of the anvil 1108 to allow for a cutting element to slide in between the stapling elements. Regardless, the example design of the sleeve 1102 allows for full functionality of the cutting and fastening elements of the surgical instrument, while still adding the additional functionality of a sealing mechanism through the electrodes 1106.

Referring to FIG. 15, a close-up view of the top side of the anvil 1108 is shown, with the sleeve 1102 attached. Also shown is a partial view of the fastening clamp 1402 to provide perspective of how the fastening clamp is connected to the rest of the sleeve 1102. FIG. 16 provides another close-up view of the proximal end of the anvil 1108. As shown, the electrode 1106 may not extend fully across the entire length of the anvil 1108. In this case, a supporting wing structure 1610 is formed into the anvil 1108 at the proximal end, providing support for when the anvil 1108 closes on to the bottom jaw, but also may limit the exposure of the electrode 1106 on the sleeve 1102. Certainly, other example implementations for a sleeve having electrodes and being adapted to slidably attached to existing jaws of a stapler surgical instrument are possible and contemplated within the scope of the present disclosures, and embodiments are not so limited.

Referring to FIG. 17, a head-on perspective view of the anvil 1108 having the attachable sleeve 1102 is shown. From this perspective, one can see an example of how the sleeve 1102 smoothly fits onto the anvil 1108. In addition, it is apparent how the electrodes 1106 are exposed on the sides of the anvil 1108. Also shown are the wing structures 1610, the cutting slot 1410, and the housing structure for the crimping divots 1404. It should be noted that the view presented in this illustration may make it difficult to appreciate a degree of depth still present in the structure of the anvil 1108. For example, the wing structures 1610 are still present only toward the proximal side of the anvil 1108, such as what is shown in FIG. 16.

Figure 18:
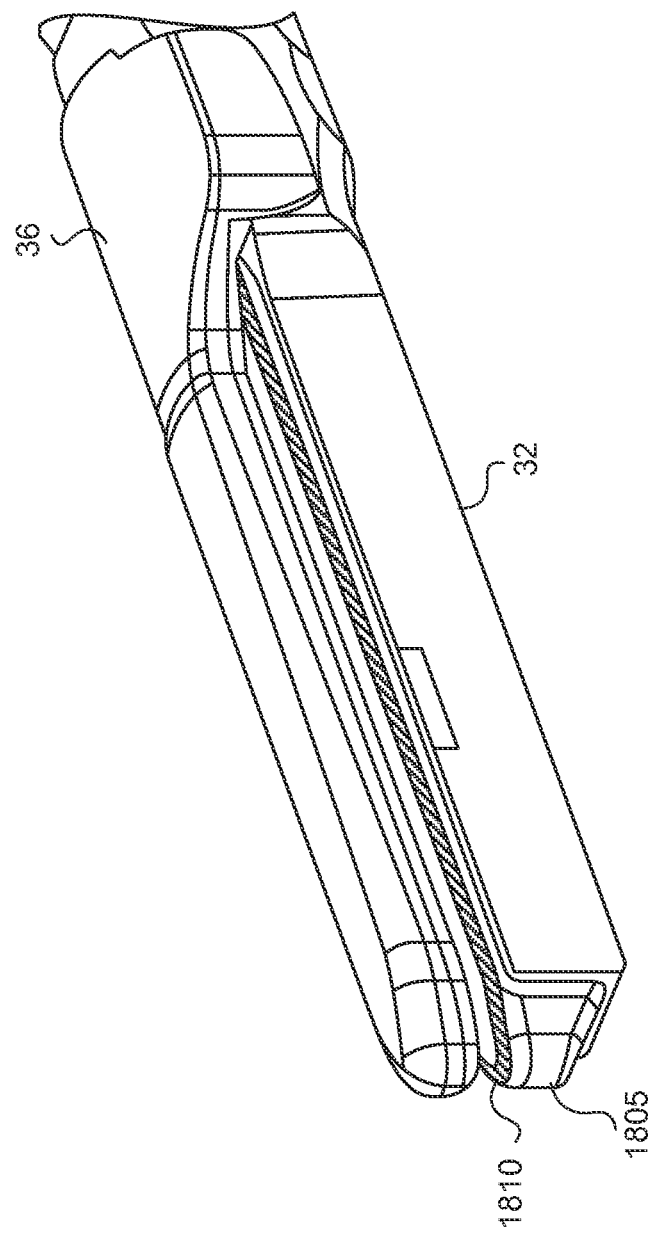
FIG. 18 shows the electrodes for coagulating in a sealing procedure may be installed in the stapler cartridge, according to some embodiments.

Referring to FIG. 18, in some embodiments, the electrodes for coagulating in a sealing procedure may be installed in the stapler cartridge. Here, the elongated channel 32 (see FIG. 1) may support installation of a specially configured staple cartridge 1805 having one or more electrodes 1810 fixedly coupled on at least one lateral edge of the staple cartridge 1805. Also shown is the anvil portion 36 in a closed position over the staple cartridge 1805 to demonstrate how the electrode 1810 may still remain exposed. In this way, existing or conventional fastening surgical instruments with stapler elements may be essentially retrofitted with additional sealing functionality to seal smaller vessels or ducts by replacing older stapler cartridges with ones that include one or more electrodes.

Figure 19:
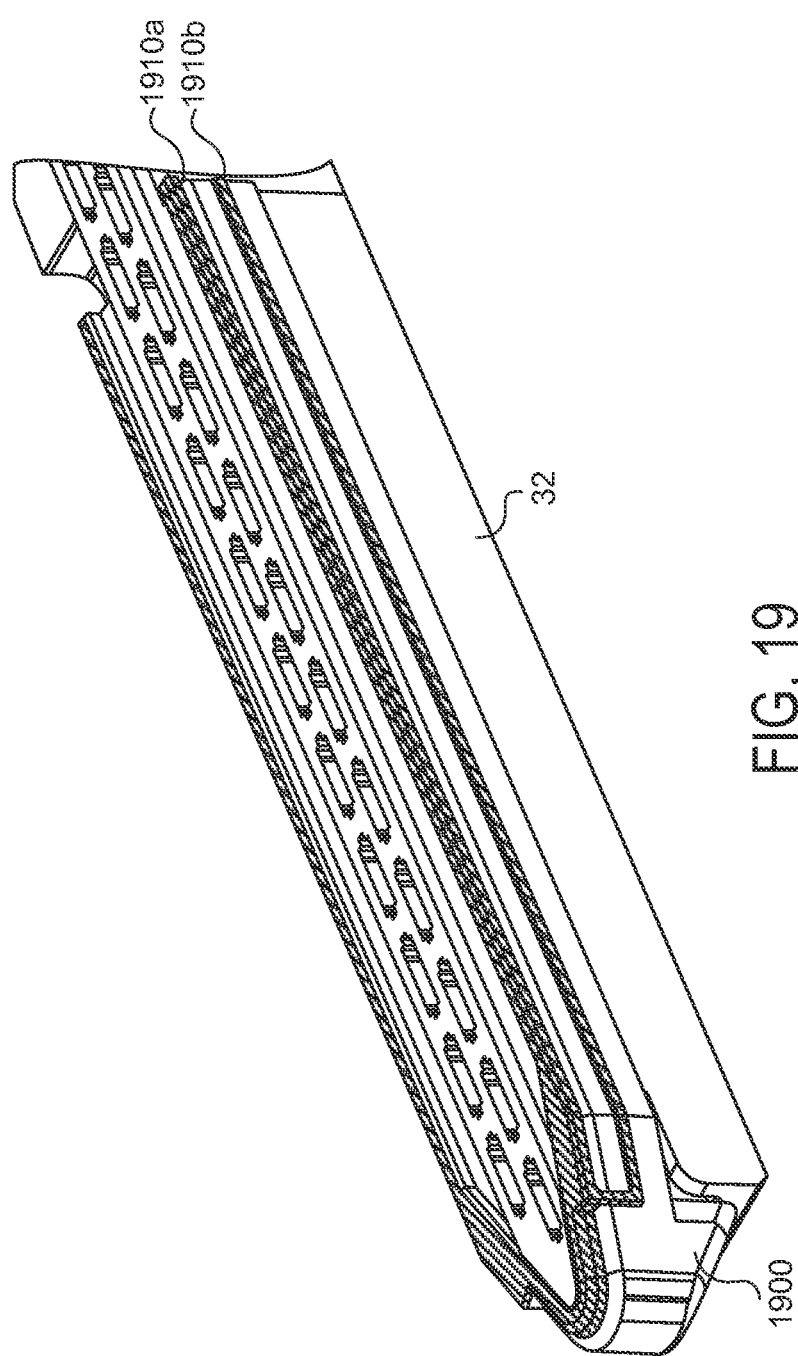
FIG. 19 shows another example implementation of a stapler cartridge coupled with electrodes, this time including a pair of wiping electrodes shown to be running in parallel along the length of the lateral sides of the stapler cartridge.

Referring to FIG. 19, another example implementation of a stapler cartridge 1900 coupled with electrodes is shown. The stapler cartridge 1900 includes a pair of wiping electrodes 1910a and 1910b, shown to be running in parallel along the length of the lateral sides of the stapler cartridge 1900. The stapler cartridge 1900 is shown to fit into the elongated channel 32. The lateral sides of the stapler cartridge 1900 may be built to extend beyond the confines of the elongated channel 32 so that the wiper electrodes 1910a in 1910b may be sufficiently exposed to touch a tissue wall at a surgical site. In other cases, the thickness of the wiping electrodes 1910a and 1910b may extend beyond the confines of the elongated channel 32.

Also shown are portions of the electrodes 1910a and 1910b that run along the top surface of the stapler cartridge 1900. In some embodiments, the electrodes may run only on the top surface or only on the lateral sides of the stapler cartridge, while in other cases a combination of both may be used, and embodiments are not so limited.

Figure 20:
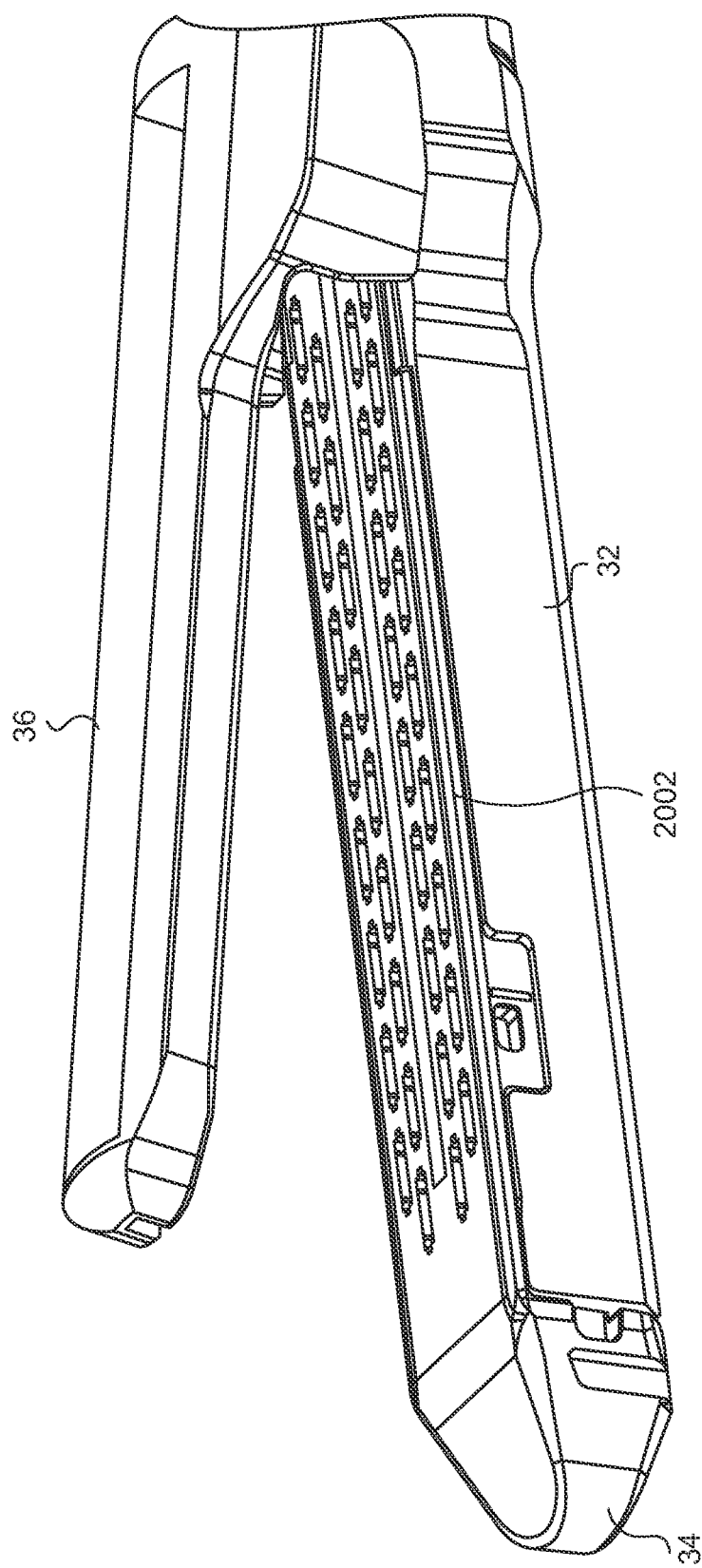
FIG. 20 shows a perspective view of an end effector having a standard or conventional removable stapler cartridge.

Referring to FIG. 20, a perspective view of an end effector having a standard or conventional removable stapler cartridge 34 is shown. FIG. 20 provides an illustration of where a side wiping electrode may be positioned to fit onto a replaceable stapler cartridge 34. For example, a cutout space 2002 located on the corner edge of the stapler cartridge 34 provides exposure just beyond the wall of the elongated channel 32. A side wiping electrode may be fitted to be placed within this cutout space 2002, as merely one example. Based on this design, the anvil 36 does not need to be redesigned or modified in order to still close onto the stapling areas of the stapler cartridge 34, while still allowing for the electrodes to be exposed to reach a tissue wall at a surgical site.

Examples of Power and Control Assemblies for Wiping Electrodes

Figure 21:
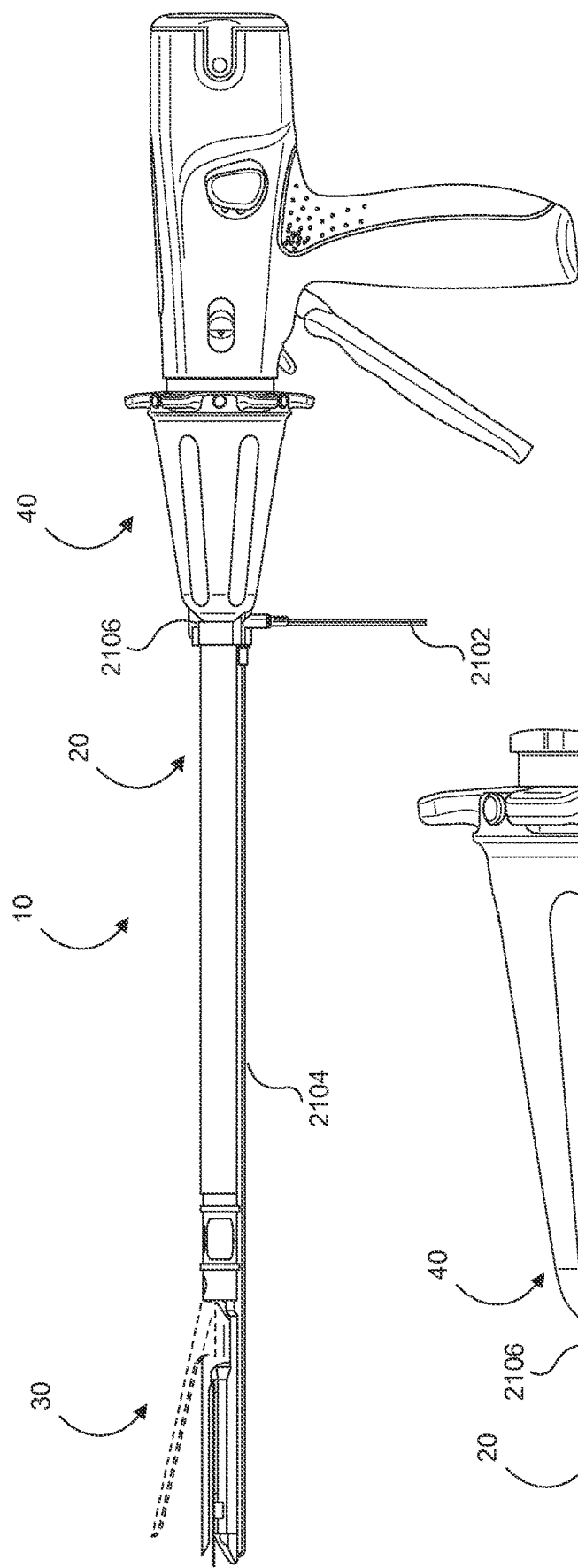
FIG. 21 shows an overall view of the surgical instrument, with the inclusion of a power and control assembly featuring a nozzle slidably attached to the shaft, according to some embodiments.

Referring to FIG. 21, an overall view of the surgical instrument 10 is revisited, here showing the inclusion of a power and control assembly featuring nozzle 40 slidably attached to the shaft 20, according to some embodiments. The nozzle 40 may include an electrical coupling connector 2106 that is coupled to the shaft 20. The connector 2106 may include ports to bridge wires 2102 and 2104 where the wires 2102 connect to a power supply, such as a power generator or a plug to an outlet of a wall socket, and the wire 2104 connects to the electrodes at the end effector 30. In some embodiments, the nozzle 40 may be slidably positioned by first ensuring that the end effector 30 is closed and then sliding the nozzle 40 over the end effector 30 and ultimately to the proximal end of the shaft 20. The slidable configuration of the nozzle 40 may enable existing surgical instruments to be essentially retrofitted with a power and control assembly for wiping electrodes positioned at various places at the end effector 30. Examples of the various positions and attachments to add the coagulation wiping functionality of the electrodes are provided in the previous figures and associated descriptions above.

Figure 22:
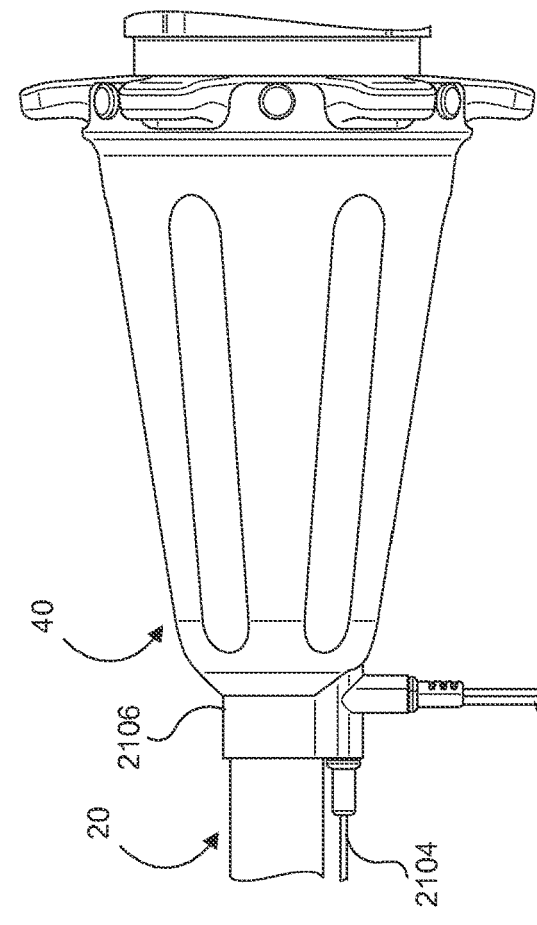
FIG. 22 shows a close-up profile view of the nozzle.

Referring to FIG. 22, a close-up profile view of the nozzle 40 is provided. Shown herein are close-up views of the coupling connector 2106, the wires 2102, and the wire 2104. In some embodiments, at least part of the nozzle 40 may be configured to rotate along the longitudinal axis of the shaft 20.

Referring to FIG. 23, a perspective view of the nozzle 40 rotated 180° along the longitudinal axis of the shaft 20 is shown. As shown, the connector 2106 is coupled to the shaft 20 and provides a bridge to wires 2302, 2304, and 2104. Of note, the two wires 2302 and 2304 are connected via plug 2312, while a single wire 2104 runs out to the electrodes at the end effector 30, not shown. One of the wires, e.g., wire 2302, may be electrically coupled to the shaft 20 to act as a ground wire, in some embodiments. Also shown are multiple grooves 2310 along the nozzle 40 to allow a user to better grip the nozzle 44 attaching to the shaft 20, and in some cases rotating the nozzle 40 in some configurations. In addition, the proximal end of the nozzle 40 may have formed finger grooves by including knobs 2306 equidistant lace based around the proximal end of the nozzle 40, as shown. A user may then control rotation of the nozzle 40 by applying torqued leverage to the knobs 2306. In some embodiments, power buttons 2308 may be included, each placed within the grooves and between the knobs 2306. The power buttons 2308 may be configured to activate the electrodes when pressed by enabling power supplied through the wires 2304 and 2104, in some embodiments. FIG. 24 provides another perspective view of the nozzle 40 in context with the surrounding shaft 20 and handle assembly 12. Shown is the closure trigger 38, configured to manipulate one or both jaws at the end effector 30, not shown. For example, a user may hold the handle assembly 12 including the trigger 38 in one hand, while still being able to control the electrodes via the power buttons 2308 on the nozzle 40 with the other hand. In some cases, both the closure trigger 38 and the nozzle 40 may be manipulated with a single hand, for example by rotating the nozzle 40 via the knobs 2306 with the user's index finger while still gripping the closure trigger and the pistol grip portion 19.

Figure 25:
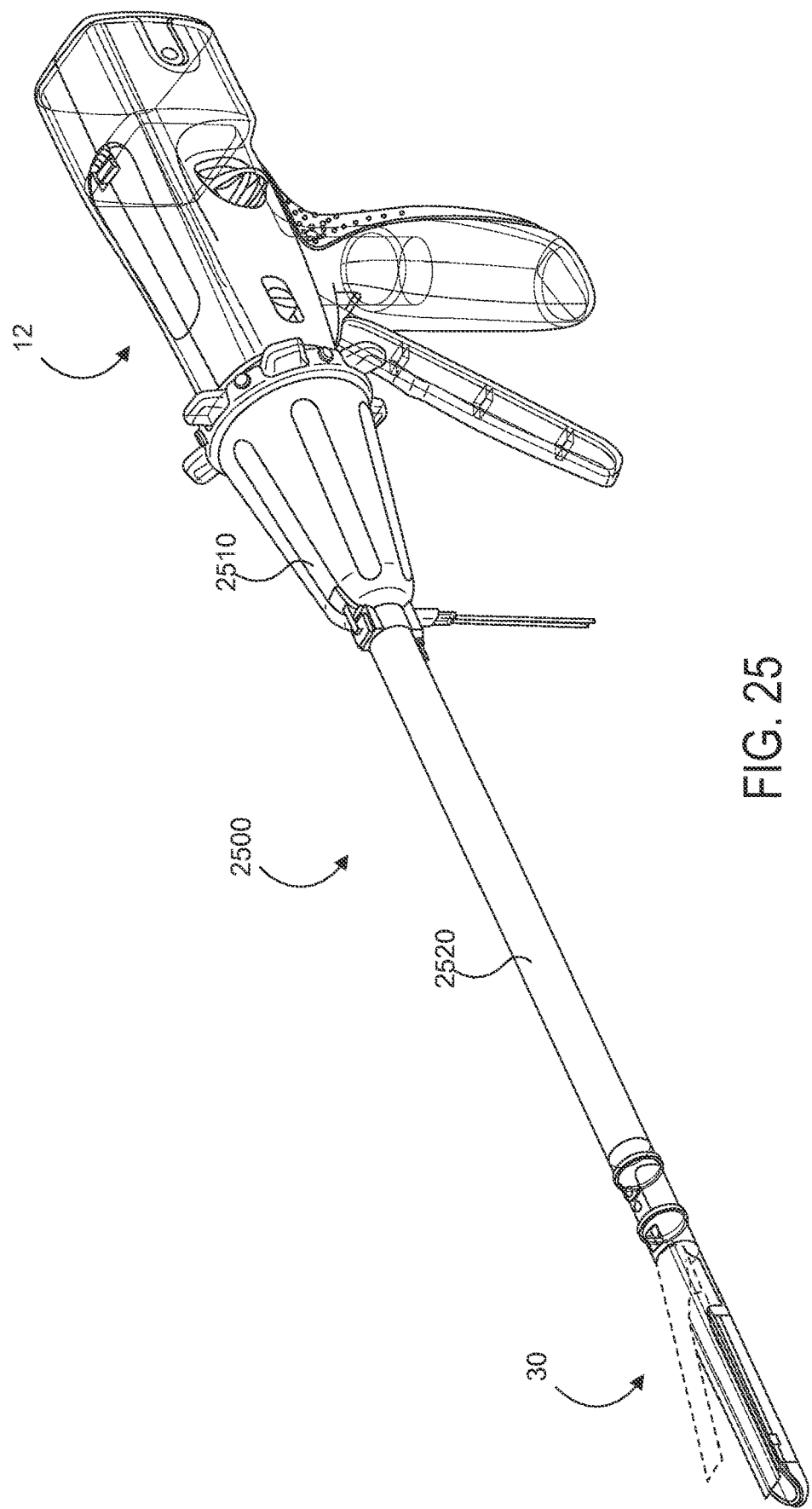
FIG. 25 illustrates an alternative power and control assembly, in this case including a slidable shaft coupled to a nozzle, all of which may be slidably attached over the shaft and coupled to the handle assembly, according to some embodiments.

Referring to FIG. 25, an alternative power and control assembly 2500 is shown, in this case including a slidable shaft 2520 coupled to a nozzle 2510, all of which may be slidably attached over the shaft 20 and coupled to the handle assembly 12, according to some embodiments. The original portions of the surgical device in this figure are drawn to be transparent, in order to distinguish the conventional surgical device from the attachable power and control assembly 2500. This design may allow for various alternatives for electrically coupling the electrodes at the end effector 30 to the shaft 2520, rather than drawing wires all the way along the shaft to the nozzle 2510.

Figure 28:
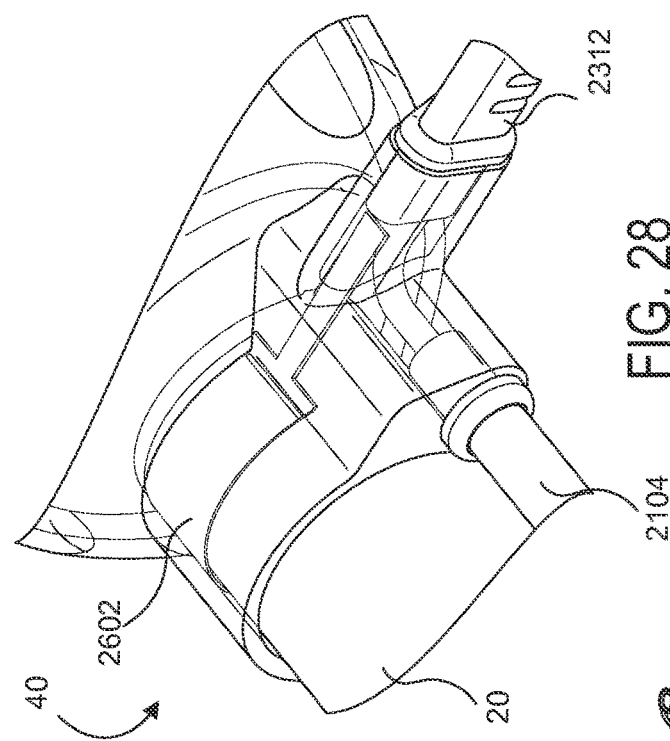
FIGS. 26-28 provide illustrations of an insert molded slidable electrical contact that allows for the power and control assembly to stably attach to the shaft while providing power to the electrodes at the end effector, according to some embodiments.
Figure 27:
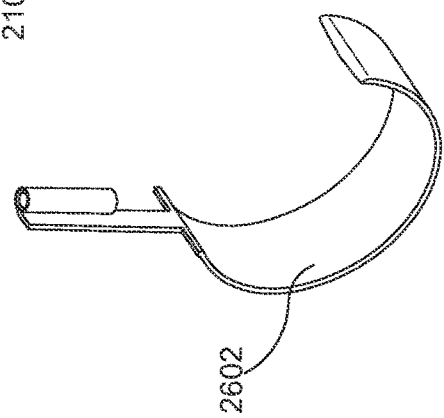
Figure 26:
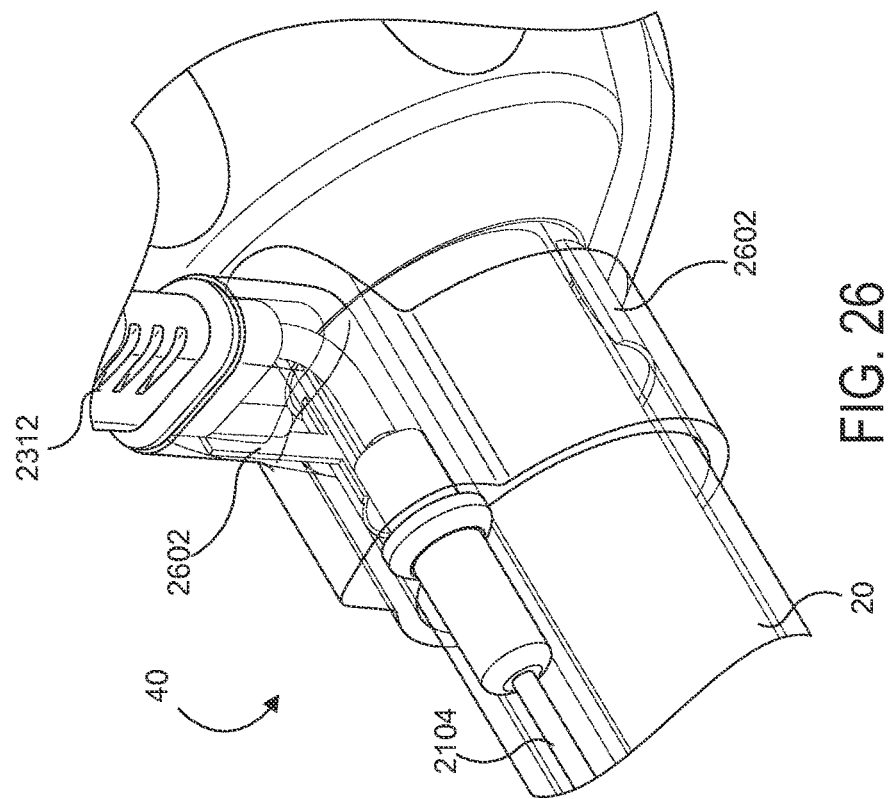

Referring to FIGS. 26-28, an insert molded slidable electrical contact 2602 is provided that allows for the power and control assembly to stably attach to the shaft 20 while providing power to the electrodes at the end effector 30, according to some embodiments. FIG. 27 shows an example design and shape of the slidable electrical contact 2602. The semicircular shape allows for the contact to slide along the shaft 20 and to ultimately snap on to the shaft 20 to stably connect the nozzle 40. The top of the electrical contact 2602 may be electrically coupled to one of the wires from the plug 2312. The electrical contact 2602 may be made of an electrically conductive material, such that the wire connected to the contacts 2602 is subsequently electrically coupled to the metal shaft 20. The electrical contact 2602 therefore may act as a grounding to the shaft 20, thereby establishing a voltage potential difference to supply power to the electrodes at the end effector 30 through the remaining wire connected through wire 2104.

FIG. 26 is an illustration showing the electrical contact 2602 in use inside the nozzle 40 portion of the power and control assembly, according to some embodiments. As shown, the top portion of the electrical contact 2602 is connected to the plug 2312, whereby one of the wires is electrically coupled to the top of the electrical contact 2602. The semicircle ring of the electrical contact 2602 is shown to be slightly detached from the shaft 20. This is to allow the power and control assembly to slide over the end effector 30 and over the shaft 20 and into place at the proximal end of the shaft 20. The electrical contact 2602 may then be snapped into place, either through a mechanical switch to pull the electrical contact 2602 and to place or through external means that constrict or tighten the surrounding contact area. Once snapped into place, the electrical contact 2602 additionally incurs the nozzle 42 the shaft 20, such that any longitudinal movements of the shaft 20 to affect closure of one or more of the jaws at the end effector 30 may be detected and measured by the power and control assembly. As described more below, measuring the distance or movement of the shaft 20 may provide variable means to determine how much power should be applied to the electrodes at the end effector 30, according to some embodiments.

FIG. 28 is an illustration showing a rotated perspective view of the electrical contact 2602 being electrically coupled to the shaft 20. As previously mentioned, one of the wires connected to the plug 2312 may be electrically coupled to the electrical contact 2602 to complete grounding to the shaft 20. Meanwhile, the other wire connected to the plug 2312 runs along the shaft 20 through the piping 2104 to electrically couple to the electrodes at the end effector 30.

Figure 30:
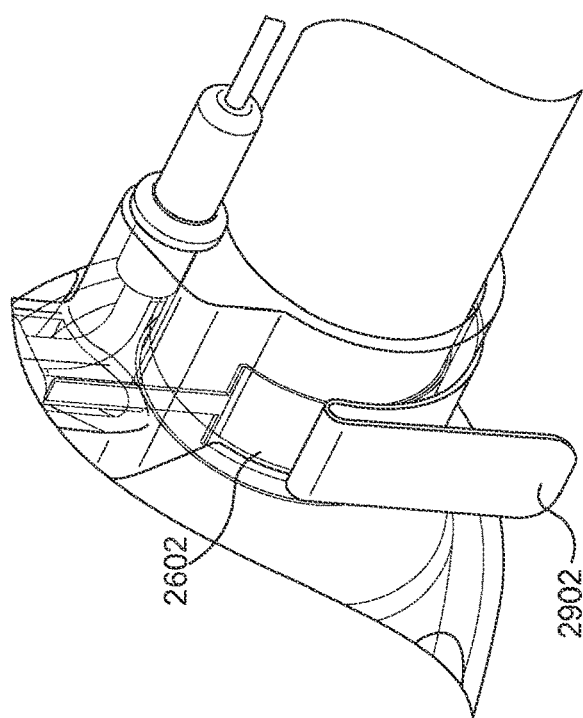
FIGS. 29-31 provide illustrations of the power and control assembly with an external clamp to help fasten or snap on the power and control assembly to the surgical instrument, according to some embodiments.
Figure 31:
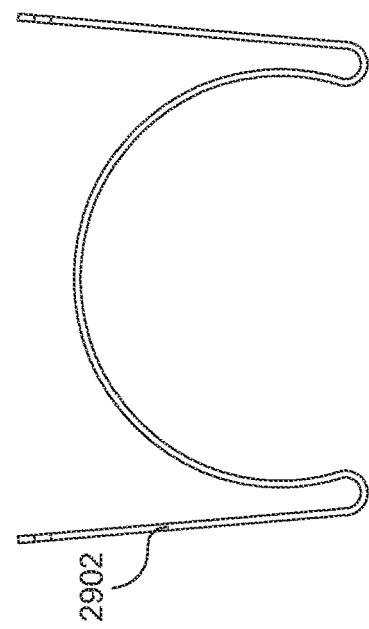
Figure 29:
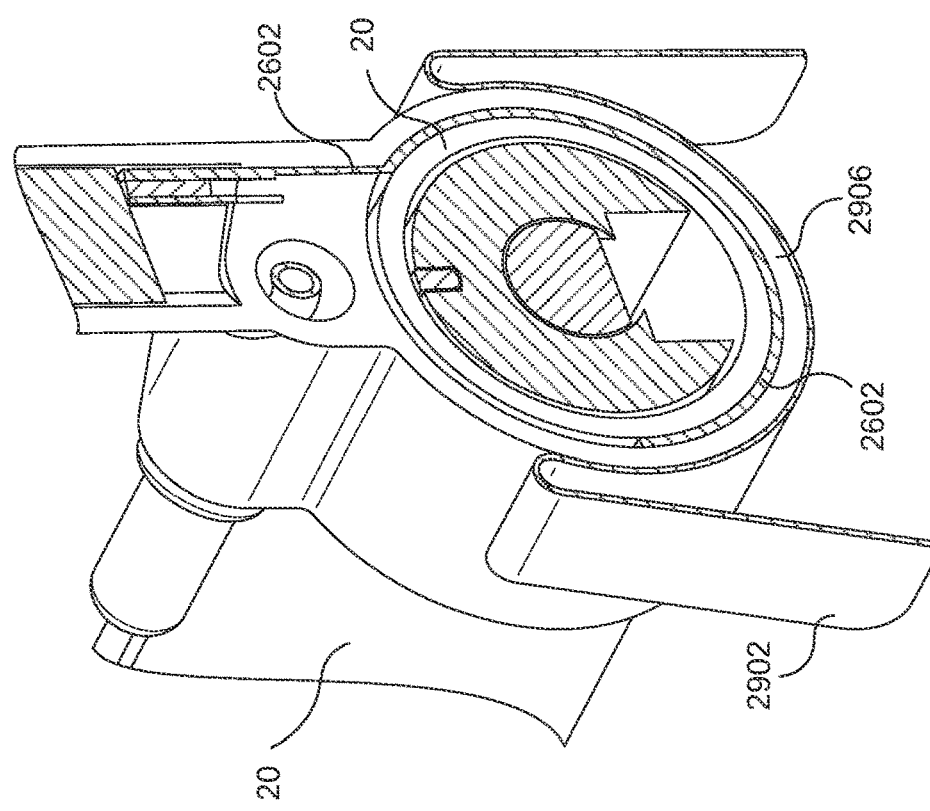

Referring to FIGS. 29-31, the power and control assembly is shown with an external clamp 2902 to help fasten or snap on the power and control assembly to the surgical instrument, according to some embodiments. FIG. 31 shows a cross-sectional view of the clamp 2902. As shown, the clamp 2902 includes a circular portion with curved ends. The circular portion is configured to wrap around the portion of the power and control assembly that includes the electrical contact 2602. The circular portion of the clamp 2902 is molded to wrap around more than 180° of the circular shaft, and is configured to be somewhat bendable, allowing for the clamp 2902 to snap into place.

FIG. 29 shows how the clamp 2902 may be applied to the electrical contact portion of the power and control assembly, according to some embodiments. A cross-sectional cutout is shown to provide detail of some of the inner workings and interactions between the shaft 20 and the electrical contact 2602 of the power and control assembly. For example, the outer casing 2906 of the power control assembly forms a thin layer covering the electrical contact 2602. The outer casing 2906 may be molded or formed to provide some space or leeway to slide along the shaft 20 before being snapped into place. Once properly positioned, the clamp 2902 may be placed around the outer casing 2906 to fasten the power and control assembly securely to the shaft 20. At this time, the electrical contact 2602 may then be fastened to be in physical contact with the shaft 20 so that the ground connection can be established. In addition, the electrical contact 2602 may be configured to slide along with the shaft 20 as the shaft is moved longitudinally to open and close at least one of the jaws of the end effector 30. This longitudinal movement of the electrical contact 2602 may be utilized to vary in amount of power applied to the electrodes, which will be described in more detail below.

Referring to FIG. 30, a semi transparent view of the power control assembly is shown, where the outer casing 2602 is made transparent to reveal the results of the clamp 2902 being fastened to the area housing the electrical contact 2602. As shown, the clamp 2902 may allow the electrical contact 2602 to be securely fastened to the shaft 20.

FIGS. 32-35 provide example views of a button 3202 configured to enable power to the electrodes at the end effector 30, according to some embodiments. For example, when the button 3202 is activated, a degree of power applied to the electrodes at the end effector 30 may be varied based on a degree of opening or closing of at least one of the jaws at the end effector 30. For example, it made be desirable to apply or allow energy to be applied to the electrodes only when the anvil is closed or substantially closed with the stapler cartridge. This may be because the clinician may desire to ensure that any sealing or coagulation procedures are capable of being performed only at the proper times. When the anvil is open or separated from the stapler cartridge, it is likely that a grasping action of the tissue is going to be performed. During this time, it therefore may not be desirable to activate the electrodes. On the other hand, once the jaws have properly grasped tissue, it may be desirable then to activate the electrodes to cause sealing in some of the targeted tissue. Thus, power to the electrodes may be applied in direct proportion to a degree of closure of the jaws. The button 3202 may be pressed, either manually or locked into place, to activate this control aspect.

Figure 33:
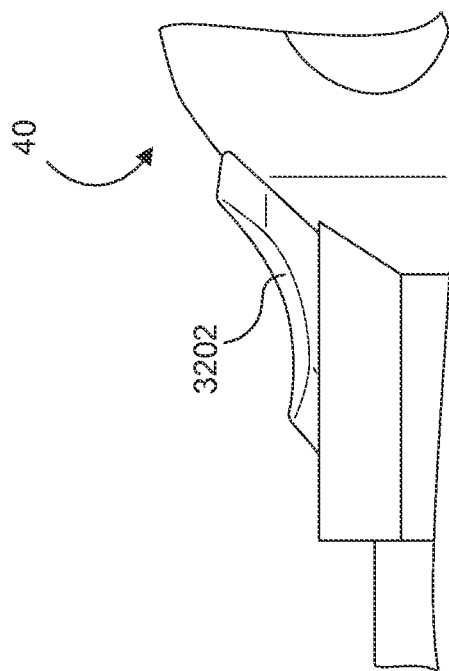
FIGS. 32-35 provide example views of a button configured to enable power to the electrodes at the end effector, according to some embodiments.
Figure 32:
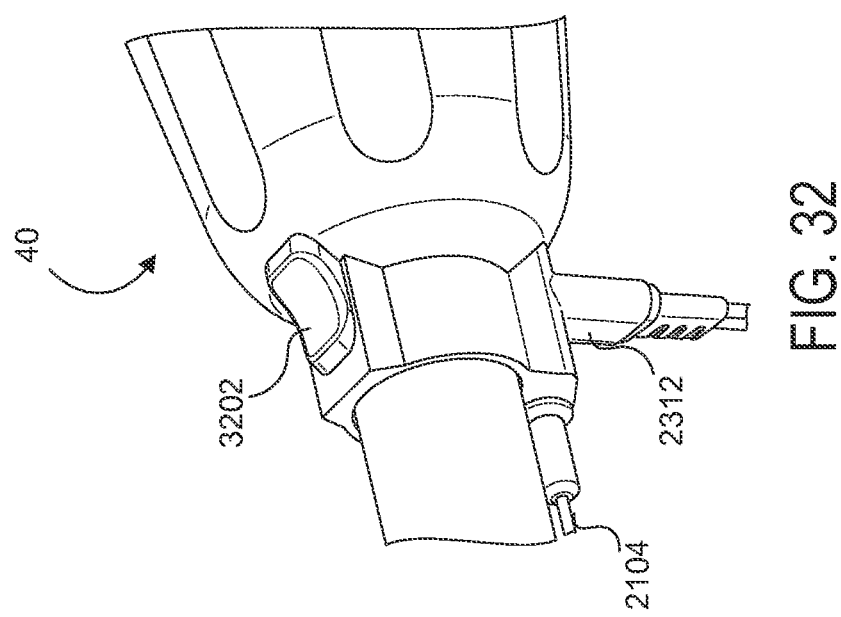
Figure 35:
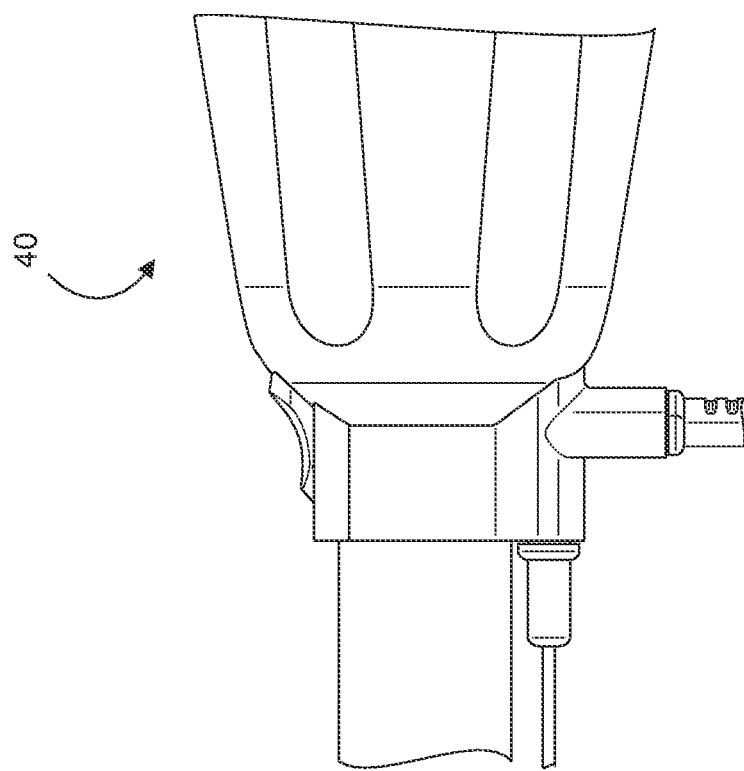

FIG. 32 shows a perspective view of the nozzle 40 having the button 3202. As shown, the clinician may press the button 3202 conveniently with his thumb or one of his fingers. FIG. 33 shows a profile view of the nozzle 40 having the button 3202. FIG. 35 shows a wider profile view of the button 3202 in the context of other components of the nozzle 40.

Figure 34:
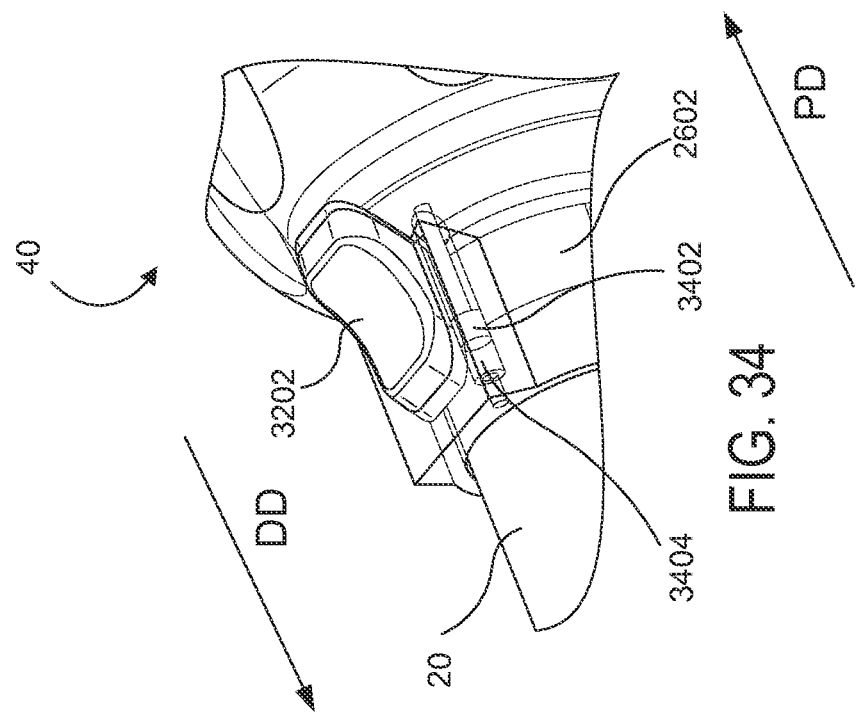

Referring to FIG. 34, a semi-transparent view of a portion of the nozzle 40 is shown to provide additional details of how the button 3202 may control power to the electrodes, according to some embodiments. Shown here is a tumbler 3402 coupled to the button 3202. The tumbler 3402 fits into a slot 3404 that allows the tumbler 3402 to slide some allowable distance. The tumbler 3402 also may be coupled to the electrical contact 2602. As previously mentioned, the electrical contact 2602 is physically and electrically coupled to the shaft 20. The shaft 20 is configured to translate back and forth longitudinally to cause opening and closing of at least one of the jaws, e.g., the anvil, of the end effector 30. Thus, when the jaws are closed, the shaft 20, and, subsequently, the tumbler 3402 coupled to the electrical contact 2602, may be translated longitudinally fully in one direction, such as in the direction DD. Conversely, when the jaws are opened, the shaft 20, and, subsequently, the tumbler 3402 coupled to the electrical contact 2602, may be translated longitudinally fully in the other direction, such as in the direction PD. When the button 3202 is pressed or locked into activation, a Hall effect sensor or other magnetic sensor within the slot 3404 may be configured to measure a distance to the tumbler 3402. A processor electrically coupled to the button 3202 and the sensor in the slot 3404 may be configured to supply power to the electrodes at the end effector 30, based on the measured distance to the tumbler 3402. The processor, not shown, may control the power supplied through the electrical contact 2602. In some cases, power applied to the electrodes may be based in direct proportion to the distance measured of the tumbler 3402. In other cases, power applied to the electrodes may be based in a more binary manner, such as power being turned on to the electrodes only when the measured distance of the tumbler 3402 satisfies a certain distance threshold, and is turned off in all other cases. In some embodiments, other energy properties of the electrodes may be controlled in proportion to the distance measured. For example, the pulse shape or the waveform of the RF energy may be varied based on the measured distance of the tumbler 3402. One form of a surgical system comprising a generator and various surgical instruments that may be employed with the motor-driven surgical cutting and fastening instrument described herein according to some embodiments, is described hereinbelow in connection with FIGS. 49 and 50.

Figure 37:
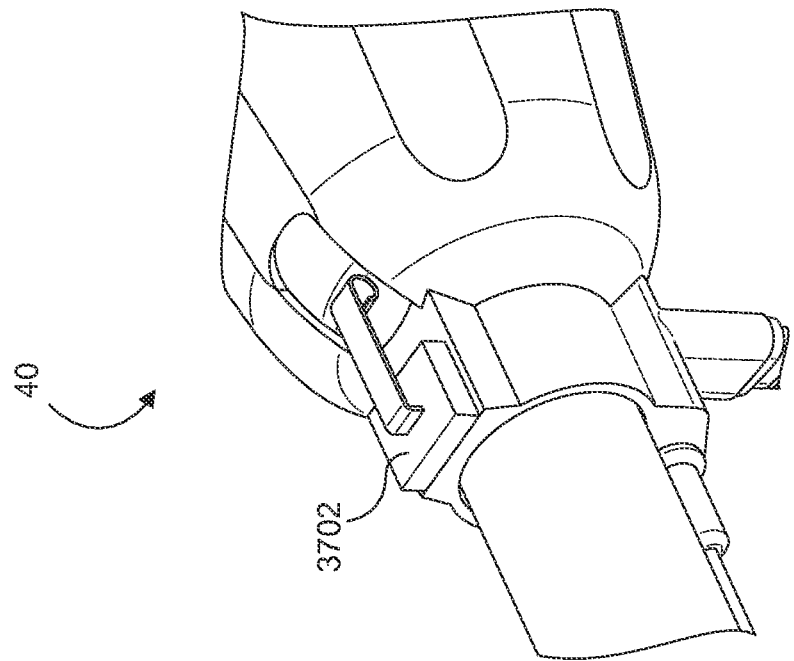
Figure 36:
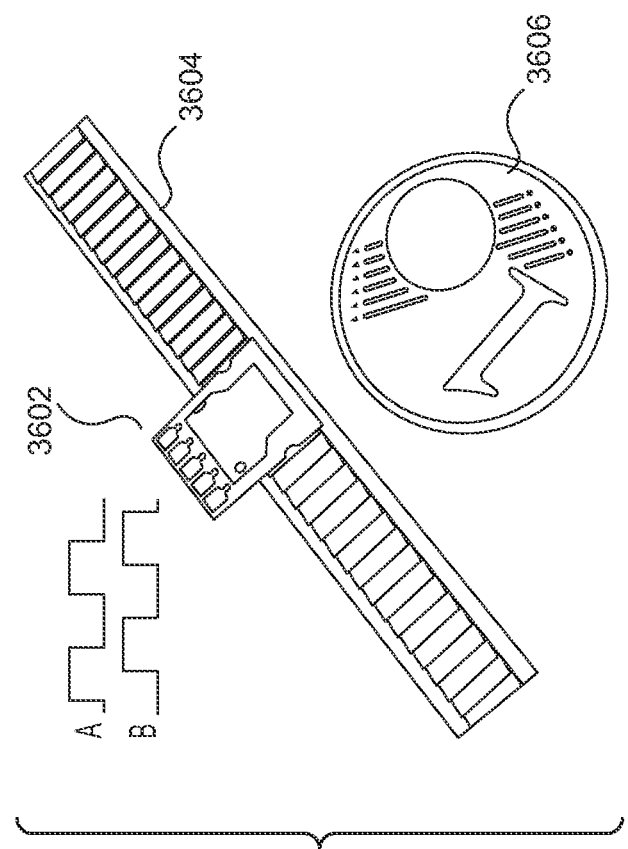
Figure 39:
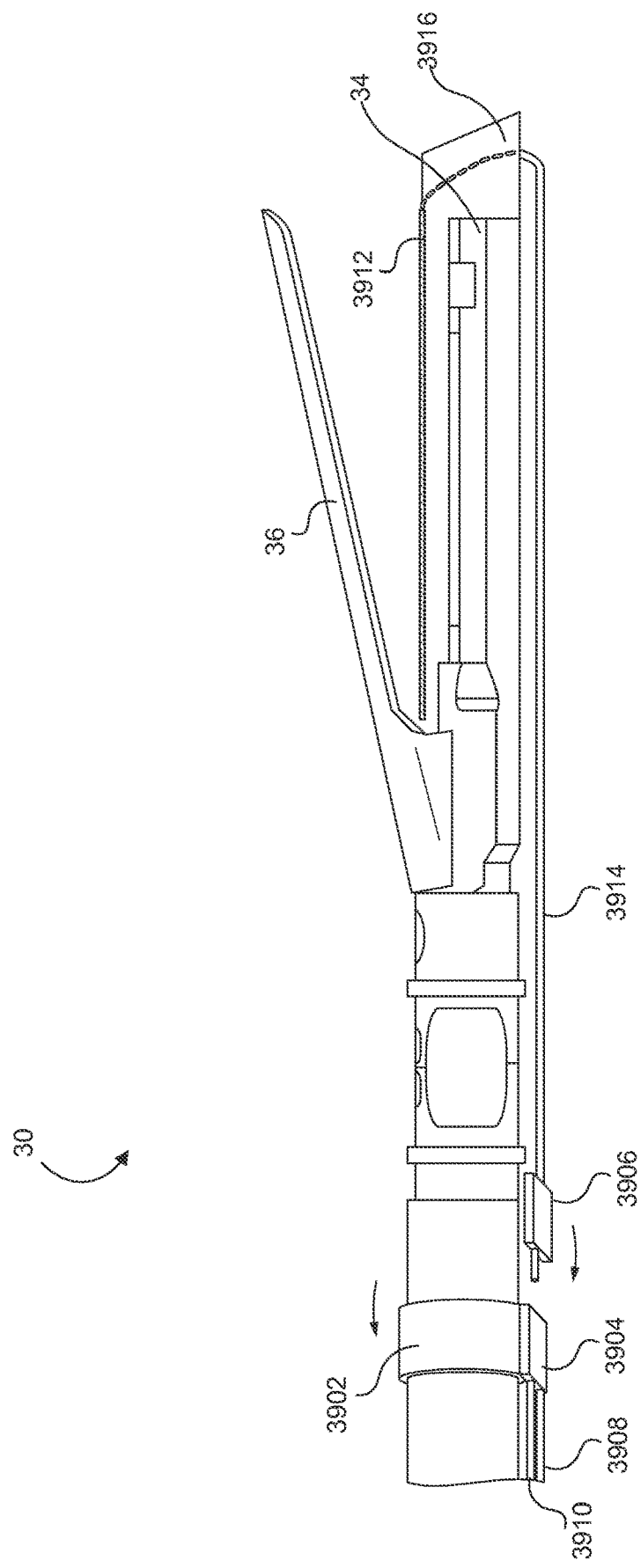
FIG. 39 provides an illustration of a band coupled to the distal end of the shaft and including an electrical connector with wires electrically coupled to the power and control assembly at the proximal end of the shaft.

Referring to FIGS. 36-38, an alternative design for varying the power applied to the electrodes is provided. For example, as shown in FIG. 36, a sensor 3602 may be placed along a measuring strip 3604. The sensor 3602 and the measuring strip 3604 may be placed within a housing 3702, as shown in FIG. 37. The sensor 3602 may be configured to slide along the strip 3604, and may be spring biased against a wall on the distal end of the nozzle 40 within the housing 3702. The sensor 3602 may be coupled to the shaft 20, such that the sensor 3602 moves along the strip 3604 as the shaft 20 is moved to open and close at least one of the jaws of the end effector 30. The strip 3604 may be electrically coupled to a processor and may be configured to vary in degree of power supplied to the electrodes based on the position of the sensor 3602 sliding along the strip 3604. In other words, energy supplied to the electrodes is varied based on displacement of the sensor 3602 along the strip 3604.

In an alternative design, referring to FIG. 38, the sensor 3602 housed in the housing 3702 may be placed in a fixed position. The sensor 3602 may be configured to measure a degree of displacement of the electrical contact 2602 as it slides under the housing 3702. Based on the measure displacement of the electrical contact 2602, a degree of jaw closure may be determined, which may subsequently guide an amount of power supplied to the electrodes.

Other slight variations utilizing components of this design includes a sliding control system that is configured to supply power to the electrodes when it is determined that the jaws are beginning to be closed and turns power off when the closure ends. As another variation, the sliding control system may be configured to turn on power to the electrodes when it is determined that the jaws are beginning to be closed and turns power off after a predetermined amount of time based on a timing procedure, regardless of the position of the jaws.

Referring to FIGS. 39-48, example apparatuses for electrically coupling the power and control assembly to the electrodes of the end effector 30 are shown. As previously mentioned, the power and control assembly may be a detachable apparatus from the existing surgical device. In addition, as previously mentioned, some embodiments include electrodes that are also detachable from the end effector, such as being included in a sleeve fitted to the anvil of the end effector or a replaceable cartridge including electrodes. In the cases where the electrodes are components of detachable apparatuses, mechanisms must be provided to electrically couple the electrodes to the detachable power and control assembly. As one example, referring to FIG. 39, a band 3902 may be coupled to the distal end of the shaft 20 and may include an electrical connector 3904 with wires 3908 and 3910 electrically coupled to the power and control assembly at the proximal end of the shaft 20, not shown. The electrical connector 3904 may be configured to connect to an electrically isolated plug 3906 that is electrically coupled to the electrodes 3912 via wire 3914. In some embodiments, a stapler cartridge 34 may include the electrodes 3912, while in other cases, a separate and detachable outer casing 3916 that includes the electrodes 3912 may be configured to wrap over a portion of the stapler cartridge 34. The wire 3914 may be configured to run along the outside of the end effector 30 so as to avoid interfering with any of the procedures that may occur between the two jaws 34 and 36.

Figure 40:
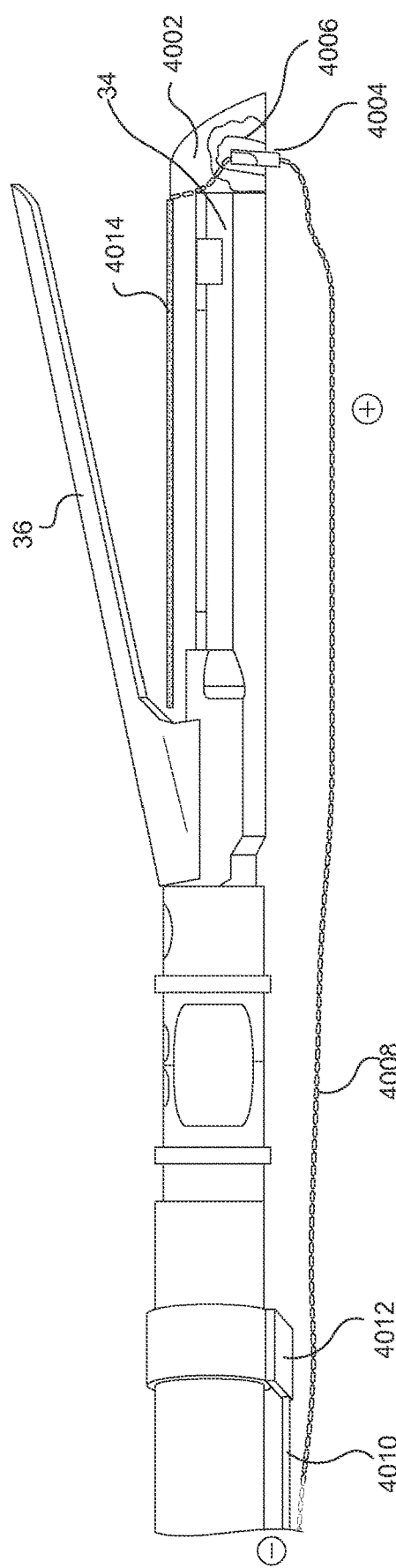
FIG. 40 shows an alternative implementation for connecting the power and control assembly to a detachable apparatus including the electrodes, in this case, including an outer cartridge housing having electrodes coupled to the cartridge.

Referring to FIG. 40, an alternative implementation for connecting the power and control assembly to a detachable apparatus including the electrodes is shown, according to some embodiments. Here, an outer cartridge housing 4002 having electrodes 4014 is coupled to the cartridge 34. The outer cartridge housing 4002 includes an outlet or other electrical connector 4006 to receive a plug 4004 connected to the power and control assembly via wire 4008. The wire 4008 may be configured to deliver RF energy having one pole, while a second wire 4010 connected to the power and control assembly having a second pole may be connected to a concentric band 4012 connecting to the shaft 20. As shown, the plug 4004 may be connected to the distal end of the housing 4002, in contrast to the location of the plug in FIG. 39. In this configuration, the apparatus that includes the electrodes 4014 need not have extra wires connected to it. In either case, the wires are shown to be positioned away from the jaws 34 and 36 so as to not interfere with any surgical procedures.

Figure 42:
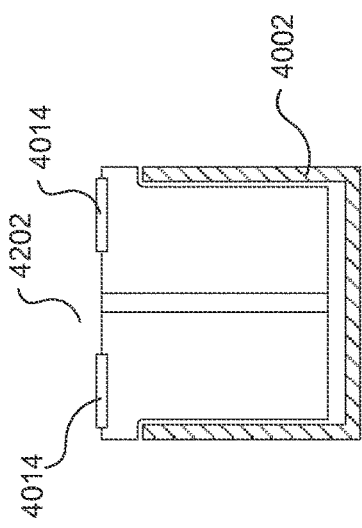
FIG. 42 shows a cross-sectional view of the electrode housing of FIG. 40.
Figure 41:
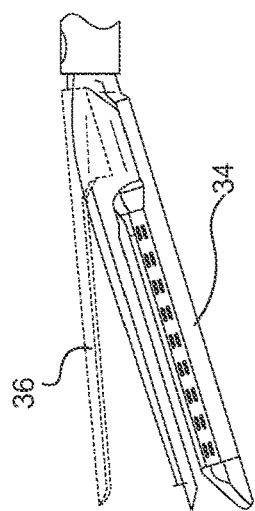
FIG. 41 illustrates that the articulation of the end effector may still be possible in the example design of FIG. 40 due to the length of the wire providing enough give to allow sufficient articulation.

FIG. 41 illustrates that the articulation of the end effector 30 may still be possible due to the length of the wire 4008 providing enough give to allow sufficient articulation. Referring to FIG. 42, a cross-sectional view of the electrode housing 4002 is shown. The electrodes 4014 may be placed sufficiently on the top and/or on the sides of the housing 4002, as shown. The housing structure 4002 allows for sufficient placement of the cartridge 34 inside. In addition, the space 4202 in between the electrodes 4014 is sufficient to enable stapling and cutting procedures.

Figure 44:
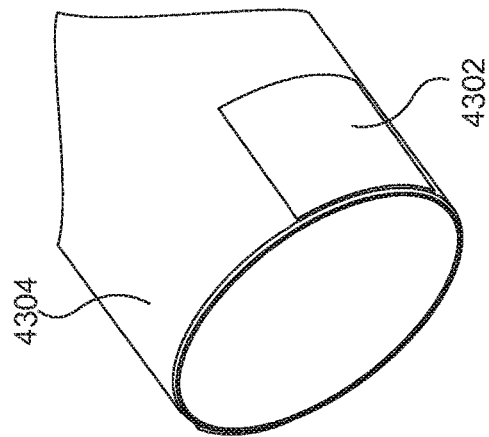
Figure 43:
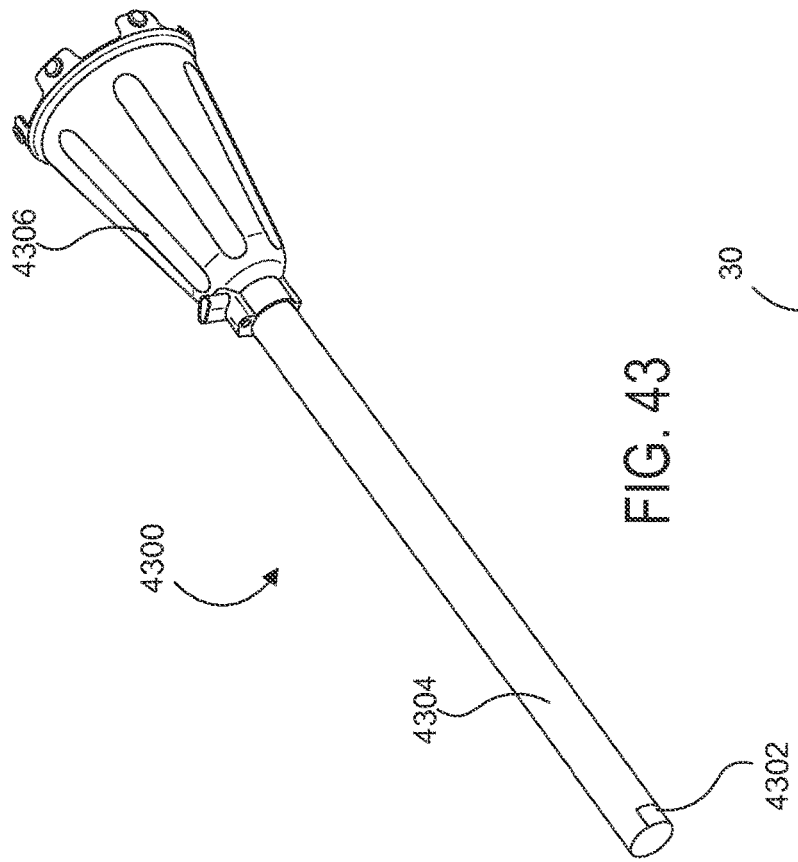

FIGS. 43-48 illustrate another alternative design to electrically connecting the electrodes at the end effector 30 to the power and control assembly, according to some embodiments. FIG. 43 shows one example of the power and control assembly 4300 including a shaft portion 4304 and a nozzle portion 4306 both configured to slide over the original shaft 20 of the surgical instrument (see FIG. 25). In addition, a conductive pad 4302 is included at the distal end of the shaft 4304 and is configured to be electrically coupled to a conductive adhesive that is part of the electrode apparatus of the end effector 30. The conductive pad 4302 may be made of copper, for example. The conductive pad 4302 may include conductive traces running along the inside of the shaft 4304 to the nozzle 4306 and other electrical components within. FIG. 44 shows a close-up perspective view of the conductive pad 4302. In some embodiments, the pad 4302 also may be placed on the other side of the shaft 4304, located 180° opposite.

Figure 45:
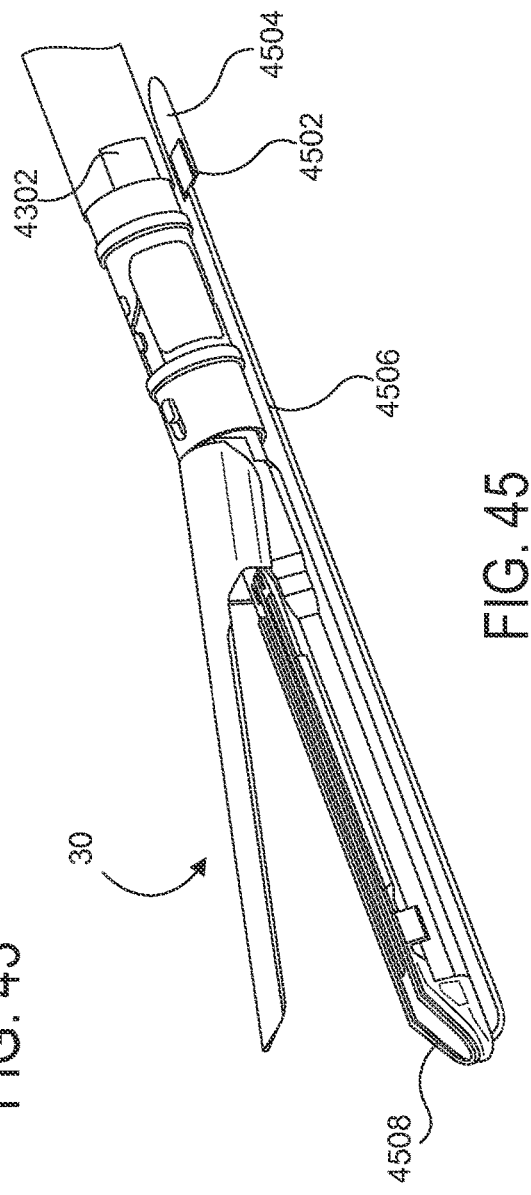

FIG. 45 shows an example of the end effector 30 having electrode 4508 and a wire 4506 coupled to a flexible conductive pad 4502. The conductive pad 4502 may be configured to attach to the shaft 4304 and the conductive pad 4302 via an adhesive pad 4504. These illustrations provide an example alternative to supplying energy to the electrodes 4508 without using a plug, such as those described in previous example embodiments.

FIG. 46 shows a close-up view of the flexible conductive pad 4502 and the associated adhesive pad 4504. Any adhesive sufficient to connect to metal may be applied. In other cases, the shaft 4304 other than the conductive pad 4302 may be made of a nonmetal or have a nonmetal coating, and the adhesive 4504 may be sufficient to adhere to the nonmetal surface. FIG. 47 shows a close-up view of the shaft 4304 having conductive pads 4302 located on opposite sides of the shaft 4304. Thus, the shaft 4304 may be rotated and may still reach sufficient connection with the conductive pad 4502. FIG. 48 shows an application of the conductive pad 4502 about to be attached to the conductive pad 4302 of the shaft 4304.

Various features described herein may be incorporated in electrosurgical devices for applying electrical energy to tissue in order to treat and/or destroy the tissue are also finding increasingly widespread applications in surgical procedures. An electrosurgical device typically includes a hand piece, an instrument having a distally-mounted end effector (e.g., one or more electrodes). The end effector can be positioned against the tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flowing through the tissue may form hemostatic seals within the tissue and/or between tissues and thus may be particularly useful for sealing blood vessels, for example. The end effector of an electrosurgical device also may include a cutting member that is movable relative to the tissue and the electrodes to transect the tissue.

Electrical energy applied by an electrosurgical device can be transmitted to the instrument by a generator in communication with the hand piece. The electrical energy may be in the form of radio frequency ("RF") energy. RF energy is a form of electrical energy that may be in the frequency range of 200 kilohertz (kHz) to 1 megahertz (MHz). In application, an electrosurgical device can transmit low frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy is useful for removing, shrinking, or sculpting soft tissue while simultaneously sealing blood vessels. RF energy works particularly well on connective tissue, which is primarily comprised of collagen and shrinks when contacted by heat.

Figure 49:
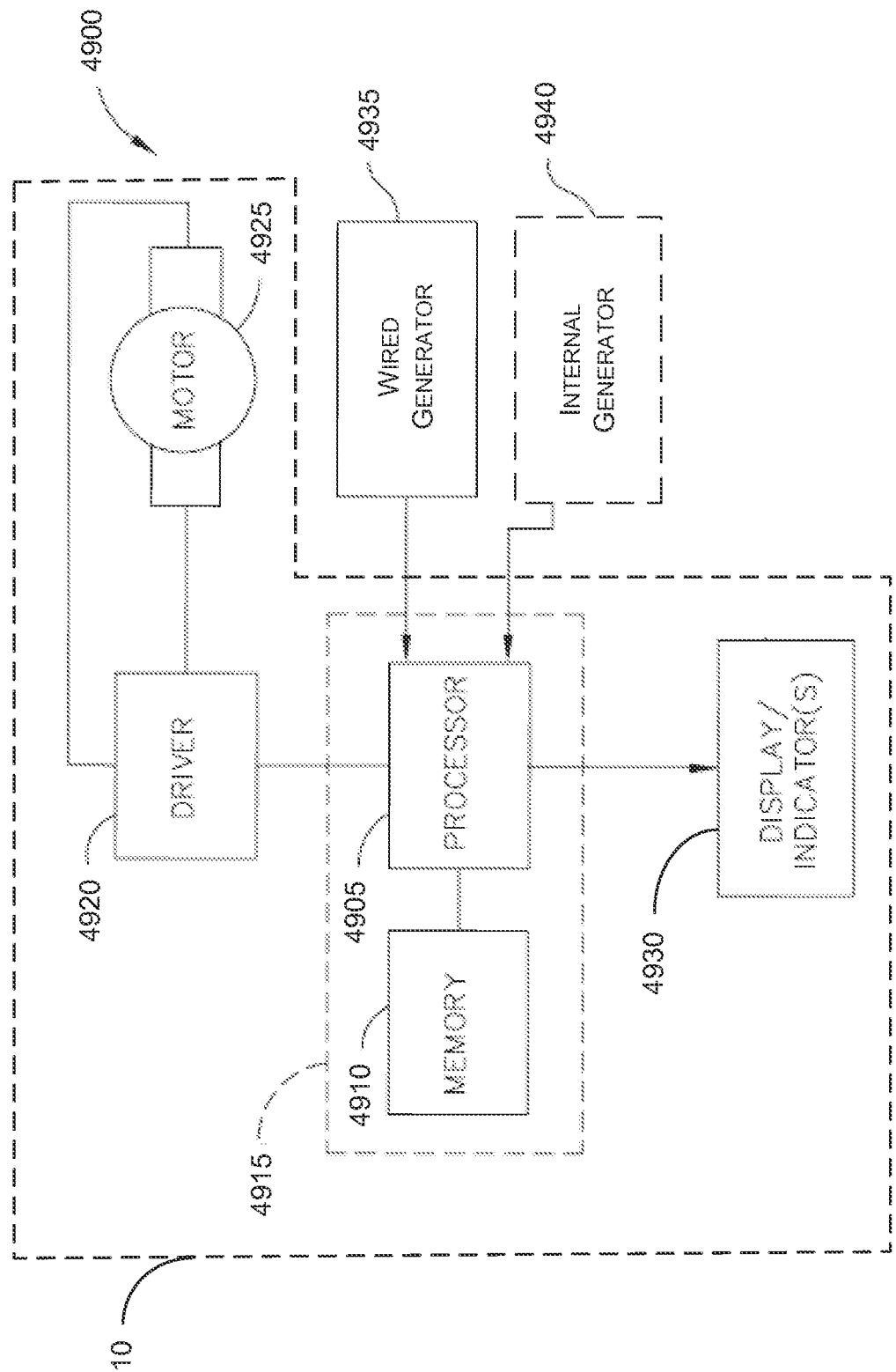
FIG. 49 is a block diagram of a surgical system comprising a motor-driven surgical cutting and fastening instrument coupled to a generator, according to some embodiments.

FIG. 49 is a block diagram of a surgical system 4900 comprising a motor-driven surgical cutting and fastening instrument 10 (FIG. 1) coupled to a generator 4935 (4940), according to some embodiments. The motor-driven surgical cutting and fastening instrument 10 described in the present disclosure, may be coupled to a generator 4935 (4940) configured to supply power to the surgical instrument through external or internal means, examples of which will be provided in more detail below. In certain instances, the motor-driven surgical cutting and fastening instrument 10 may include a microcontroller 4915 coupled to an external wired generator 4935 or internal generator 4940. Either the external generator 4935 or the internal generator 4940 may be coupled to A/C mains or may be battery operated or combinations thereof. The electrical and electronic circuit elements associated with the motor-driven surgical cutting and fastening instrument 10 and/or the generator elements 4935, 4940 may be supported by a control circuit board assembly, for example. The microcontroller 4915 may generally comprise a memory 4910 and a microprocessor 4905 ("processor") operationally coupled to the memory 4910. The processor 4905 may control a motor driver 4920 circuit generally utilized to control the position and velocity of the motor 4925. The motor 4925 may be configured to control transmission of energy to the electrodes at the end effector of the surgical instrument. In certain instances, the processor 4905 can signal the motor driver 4920 to stop and/or disable the motor 4925, as described in greater detail below. In certain instances, the processor 4905 may control a separate motor override circuit which may comprise a motor override switch that can stop and/or disable the motor 4925 during operation of the surgical instrument in response to an override signal from the processor 4905. It should be understood that the term processor as used herein includes any suitable microprocessor, microcontroller, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In some cases, the processor 4905 may be any single core or multicore processor such as those known under the trade name ARM Cortex by Texas Instruments. In some cases, any of the surgical instruments of the present disclosures may comprise a safety processor such as, for example, a safety microcontroller platform comprising two microcontroller-based families such as TMS570 and RM4x known under the trade name Hercules ARM Cortex R4, also by Texas Instruments. Nevertheless, other suitable substitutes for microcontrollers and safety processor may be employed, without limitation. In one instance, the safety processor may be configured specifically for IEC 61508 and ISO 26262 safety critical applications, among others, to provide advanced integrated safety features while delivering scalable performance, connectivity, and memory options.

In certain instances, the microcontroller 4915 may be an LM 4F230H5QR, available from Texas Instruments, for example. In at least one example, the Texas Instruments LM4F230H5QR is an ARM Cortex-M4F Processor Core comprising on-chip memory 4910 of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet. Other microcontrollers may be readily substituted for use in the motor-driven surgical cutting and fastening instrument 10. Accordingly, the present disclosure should not be limited in this context.

Referring again to FIG. 49, the surgical system 4900 may include a wired generator 4935, for example. In certain instances, the wired generator 4935 may be configured to supply power through external means, such as through electrical wire coupled to an external generator. In some cases, the surgical system 4900 also may include or alternatively include an internal generator 4940. The internal generator 4940 may be configured to supply power through internal means, such as through battery power or other stored capacitive source. Further descriptions of the internal generator 4940 and the wired generator 4935 are described below.

In certain instances, the motor-driven surgical cutting and fastening instrument 10 may comprise one or more embedded applications implemented as firmware, software, hardware, or any combination thereof. In certain instances, the motor-driven surgical cutting and fastening instrument 10 may comprise various executable modules such as software, programs, data, drivers, and/or application program interfaces (APIs), for example.

Figure 50:
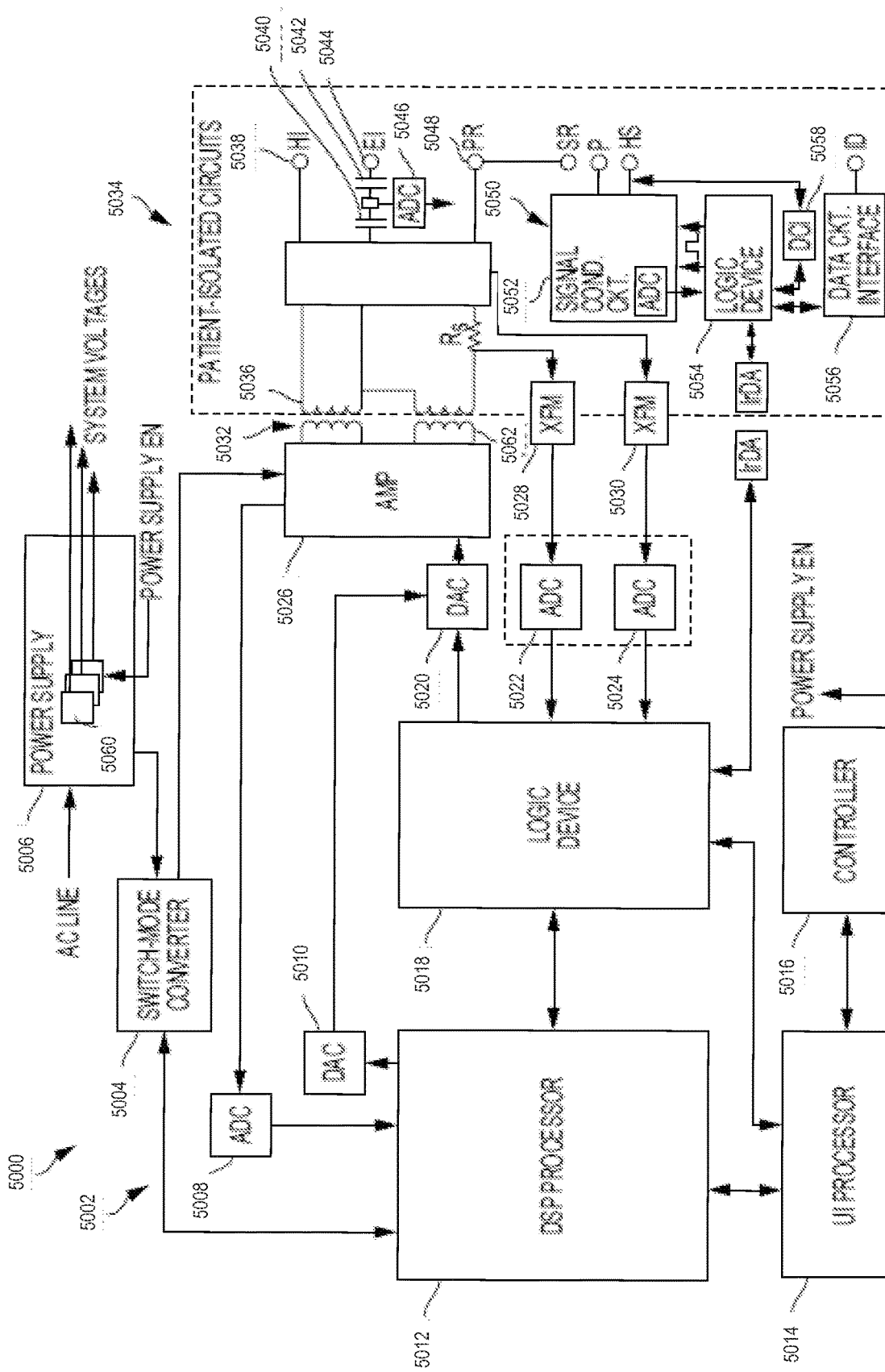
FIG. 50 is a simplified block diagram of one form of the wired generator in FIG. 49 for providing inductorless tuning, according to some embodiments.

FIG. 50 is a simplified block diagram 5000 of one form of the generator 4935 for providing inductorless tuning as described above, among other benefits. Additional details of the generator 4935 are described in commonly assigned and contemporaneously filed U.S. patent application Ser. No. 12/896,360, titled "Surgical Generator For Ultrasonic And Electrosurgical Devices," the disclosure of which is incorporated herein by reference in its entirety. With reference to FIG. 50, the generator 5000 may comprise a patient isolated stage 5034 in communication with a non-isolated stage 5002 via a power transformer 5032. A secondary winding 5036 of the power transformer 5032 is contained in the isolated stage 5034 and may comprise a tapped configuration (e.g., a center-tapped or a non-center-tapped configuration) to define drive signal outputs 5038, 5044, 5048 for outputting drive signals to different surgical devices, such as, for example, a surgical device 10 having an end effector with electrodes like in FIG. 2 and a different surgical device having an end effector with electrodes like in FIG. 4. In particular, drive signal outputs 5044, 5048 may output an electrosurgical drive signal (e.g., a 100V RMS drive signal) to a power and control assembly 40, with output 5044 corresponding to the center tap of the power transformer 5032.

The non-isolated stage 5002 may comprise a power amplifier 5026 having an output connected to a primary winding 5062 of the power transformer 5032. In certain forms the power amplifier 5026 may be comprise a push-pull amplifier. For example, the non-isolated stage 5002 may further comprise a logic device 5018 for supplying a digital output to a digital-to-analog converter (DAC) 5020, which in turn supplies a corresponding analog signal to an input of the power amplifier 5026. In certain forms the logic device 5018 may comprise a programmable gate array (PGA), a field-programmable gate array (FPGA), programmable logic device (PLD), among other logic circuits, for example. The logic device 5018, by virtue of controlling the input of the power amplifier 5026 via the DAC 5020, may therefore control any of a number of parameters (e.g., frequency, waveform shape, waveform amplitude) of drive signals appearing at the drive signal outputs 5038, 5044, 5048. In certain forms and as discussed below, the logic device 5018, in conjunction with a processor (e.g., a digital signal processor discussed below), may implement a number of digital signal processing (DSP)-based and/or other control algorithms to control parameters of the drive signals output by the generator 5000.

Power may be supplied to a power rail of the power amplifier 5026 by a switch-mode regulator 5004. In certain forms the switch-mode regulator 5004 may comprise an adjustable buck regulator, for example. The non-isolated stage 5002 may further comprise a first processor 5012, which in one form may comprise a DSP processor such as an Analog Devices ADSP-21469 SHARC DSP, available from Analog Devices, Norwood, Mass., for example, although in various forms any suitable processor may be employed. In certain forms the processor 5012 may control operation of the switch-mode power converter 5004 responsive to voltage feedback data received from the power amplifier 5026 by the DSP processor 5012 via an analog-to-digital converter (ADC) 5008. In one form, for example, the DSP processor 5012 may receive as input, via the ADC 5008, the waveform envelope of a signal (e.g., an RF signal) being amplified by the power amplifier 5026. The DSP processor 5012 may then control the switch-mode regulator 5004 (e.g., via a pulse-width modulated (PWM) output) such that the rail voltage supplied to the power amplifier 5026 tracks the waveform envelope of the amplified signal. By dynamically modulating the rail voltage of the power amplifier 5026 based on the waveform envelope, the efficiency of the power amplifier 5026 may be significantly improved relative to a fixed rail voltage amplifier schemes.

In certain forms, the logic device 5018, in conjunction with the DSP processor 5012, may implement a direct digital synthesizer (DDS) control scheme to control the waveform shape, frequency and/or amplitude of drive signals output by the generator 5000. In one form, for example, the logic device 5018 may implement a DDS control algorithm by recalling waveform samples stored in a dynamically-updated look-up table (LUT), such as a RAM LUT, which may be embedded in an FPGA. Because the waveform shape of a drive signal output by the generator 5000 is impacted by various sources of distortion present in the output drive circuit (e.g., the power transformer 5032, the power amplifier 5026), voltage and current feedback data based on the drive signal may be input into an algorithm, such as an error control algorithm implemented by the DSP processor 5012, which compensates for distortion by suitably pre-distorting or modifying the waveform samples stored in the LUT on a dynamic, ongoing basis (e.g., in real-time). In one form, the amount or degree of pre-distortion applied to the LUT samples may be based on the error between a computed motional branch current and a desired current waveform shape, with the error being determined on a sample-by-sample basis. In this way, the pre-distorted LUT samples, when processed through the drive circuit, may result in a motional branch drive signal having the desired waveform shape (e.g., sinusoidal) for optimally driving the ultrasonic transducer. In such forms, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 5002 may further comprise an ADC 5022 and an ADC 5024 coupled to the output of the power transformer 5032 via respective isolation transformers 5028, 5030 for respectively sampling the voltage and current of drive signals output by the generator 5000. In certain forms, the ADCs 5022, 5024 may be configured to sample at high speeds (e.g., 80 MSPS) to enable oversampling of the drive signals. In one form, for example, the sampling speed of the ADCs 5022, 5024 may enable approximately 200× (depending on frequency) oversampling of the drive signals. In certain forms, the sampling operations of the ADC 5022, 5024 may be performed by a singe ADC receiving input voltage and current signals via a two-way multiplexer. The use of high-speed sampling in forms of the generator 5000 may enable, among other things, calculation of the complex current flowing through the motional branch (which may be used in certain forms to implement DDS-based waveform shape control described above), accurate digital filtering of the sampled signals, and calculation of real power consumption with a high degree of precision. Voltage and current feedback data output by the ADCs 5022, 5024 may be received and processed (e.g., FIFO buffering, multiplexing) by the logic device 5018 and stored in data memory for subsequent retrieval by, for example, the DSP processor 5012. As noted above, voltage and current feedback data may be used as input to an algorithm for pre-distorting or modifying LUT waveform samples on a dynamic and ongoing basis. In certain forms, this may require each stored voltage and current feedback data pair to be indexed based on, or otherwise associated with, a corresponding LUT sample that was output by the logic device 5018 when the voltage and current feedback data pair was acquired. Synchronization of the LUT samples and the voltage and current feedback data in this manner contributes to the correct timing and stability of the pre-distortion algorithm.

In certain forms, the voltage and current feedback data may be used to control the frequency and/or amplitude (e.g., current amplitude) of the drive signals. In one form, for example, voltage and current feedback data may be used to determine impedance phase. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy. The determination of phase impedance and a frequency control signal may be implemented in the DSP processor 5012, for example, with the frequency control signal being supplied as input to a DDS control algorithm implemented by the logic device 5018.

In another form, for example, the current feedback data may be monitored in order to maintain the current amplitude of the drive signal at a current amplitude setpoint. The current amplitude setpoint may be specified directly or determined indirectly based on specified voltage amplitude and power setpoints. In certain forms, control of the current amplitude may be implemented by control algorithm, such as, for example, a PID control algorithm, in the processor 5012. Variables controlled by the control algorithm to suitably control the current amplitude of the drive signal may include, for example, the scaling of the LUT waveform samples stored in the logic device 5018 and/or the full-scale output voltage of the DAC 5020 (which supplies the input to the power amplifier 5026) via a DAC 5010.

The non-isolated stage 5002 may further comprise a second processor 5014 for providing, among other things user interface (UI) functionality. In one form, the UI processor 5014 may comprise an Atmel AT91SAM9263 processor having an ARM 926EJ-S core, available from Atmel Corporation, San Jose, Calif., for example. Examples of UI functionality supported by the UI processor 5014 may include audible and visual user feedback, communication with peripheral devices (e.g., via a Universal Serial Bus (USB) interface), communication with a footswitch, communication with an input device (e.g., a touch screen display indicators 4930) and communication with an output device (e.g., a speaker). The UI processor 5014 may communicate with the processor 5012 and the logic device 5018 (e.g., via serial peripheral interface (SPI) buses). Although the UI processor 5014 may primarily support UI functionality, it also may coordinate with the DSP processor 5012 to implement hazard mitigation in certain forms. For example, the UI processor 5014 may be programmed to monitor various aspects of user input and/or other inputs (e.g., touch screen inputs, footswitch inputs, temperature sensor inputs) and may disable the drive output of the generator 5000 when an erroneous condition is detected.

In certain forms, both the DSP processor 5012 and the UI processor 5014, for example, may determine and monitor the operating state of the generator 5000. For the DSP processor 5012, the operating state of the generator 5000 may dictate, for example, which control and/or diagnostic processes are implemented by the DSP processor 5012. For the UI processor 5014, the operating state of the generator 5000 may dictate, for example, which elements of a user interface (e.g., display screens, sounds) are presented to a user. The respective DSP and UI processors 5012, 5014 may independently maintain the current operating state of the generator 5000 and recognize and evaluate possible transitions out of the current operating state. The DSP processor 5012 may function as the master in this relationship and determine when transitions between operating states are to occur. The UI processor 5014 may be aware of valid transitions between operating states and may confirm if a particular transition is appropriate. For example, when the DSP processor 5012 instructs the UI processor 5014 to transition to a specific state, the UI processor 5014 may verify that requested transition is valid. In the event that a requested transition between states is determined to be invalid by the UI processor 5014, the UI processor 5014 may cause the generator 5000 to enter a failure mode.

The non-isolated stage 5002 may further comprise a controller 5016 for monitoring input devices (e.g., a capacitive touch sensor used for turning the generator 5000 on and off, a capacitive touch screen). In certain forms, the controller 5016 may comprise at least one processor and/or other controller device in communication with the UI processor 5014. In one form, for example, the controller 5016 may comprise a processor (e.g., a Mega168 8-bit controller available from Atmel) configured to monitor user input provided via one or more capacitive touch sensors. In one form, the controller 5016 may comprise a touch screen controller (e.g., a QT5480 touch screen controller available from Atmel) to control and manage the acquisition of touch data from a capacitive touch screen.

In certain forms, when the generator 5000 is in a "power off" state, the controller 5016 may continue to receive operating power (e.g., via a line from a power supply of the generator 5000). In this way, the controller 5016 may continue to monitor an input device (e.g., a capacitive touch sensor located on a front panel of the generator 5000) for turning the generator 5000 on and off. When the generator 5000 is in the power off state, the controller 5016 may wake the power supply (e.g., enable operation of one or more DC/DC voltage converters 5060 of the power supply 5006) if activation of the "on/off" input device by a user is detected. The controller 5016 may therefore initiate a sequence for transitioning the generator 5000 to a "power on" state. Conversely, the controller 5016 may initiate a sequence for transitioning the generator 5000 to the power off state if activation of the "on/off" input device is detected when the generator 5000 is in the power on state. In certain forms, for example, the controller 5016 may report activation of the "on/off" input device to the processor 5014, which in turn implements the necessary process sequence for transitioning the generator 5000 to the power off state. In such forms, the controller 5016 may have no independent ability for causing the removal of power from the generator 5000 after its power on state has been established.

In certain forms, the controller 5016 may cause the generator 5000 to provide audible or other sensory feedback for alerting the user that a power on or power off sequence has been initiated. Such an alert may be provided at the beginning of a power on or power off sequence and prior to the commencement of other processes associated with the sequence.

In certain forms, the isolated stage 5034 may comprise an instrument interface circuit 5050 to, for example, provide a communication interface between a control circuit of a surgical device (e.g., a control circuit comprising hand piece switches) and components of the non-isolated stage 5002, such as, for example, the programmable logic device 5018, the DSP processor 5012 and/or the UI processor 5014. The instrument interface circuit 5050 may exchange information with components of the non-isolated stage 5002 via a communication link that maintains a suitable degree of electrical isolation between the stages 5034, 5002, such as, for example, an infrared (IR)-based communication link. Power may be supplied to the instrument interface circuit 5050 using, for example, a low-dropout voltage regulator powered by an isolation transformer driven from the non-isolated stage 5002.

In one form, the instrument interface circuit 5050 may comprise a logic device 5054 (e.g., logic circuit, programmable logic circuit, PGA, FPGA, PLD) in communication with a signal conditioning circuit 5052. The signal conditioning circuit 5052 may be configured to receive a periodic signal from the logic circuit 5054 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical device control circuit (e.g., by using a conductive pair in a cable that connects the generator 5000 to the surgical device) and monitored to determine a state or configuration of the control circuit. The control circuit may comprise a number of switches, resistors and/or diodes to modify one or more characteristics (e.g., amplitude, rectification) of the interrogation signal such that a state or configuration of the control circuit is uniquely discernable based on the one or more characteristics. In one form, for example, the signal conditioning circuit 5052 may comprises an ADC for generating samples of a voltage signal appearing across inputs of the control circuit resulting from passage of interrogation signal therethrough. The logic device 5054 (or a component of the non-isolated stage 5002) may then determine the state or configuration of the control circuit based on the ADC samples.

In one form, the instrument interface circuit 5050 may comprise a first data circuit interface 5056 to enable information exchange between the logic circuit 5054 (or other element of the instrument interface circuit 5050) and a first data circuit disposed in or otherwise associated with a surgical device. In certain forms, for example, a first data circuit may be disposed in a cable integrally attached to a surgical device hand piece, or in an adaptor for interfacing a specific surgical device type or model with the generator 5000. The data circuit may be implemented in any suitable manner and may communicate with the generator according to any suitable protocol. In certain forms, the first data circuit may comprise a non-volatile storage device, such as an electrically erasable programmable read-only memory (EEPROM) device. In certain forms, the first data circuit interface 5056 may be implemented separately from the logic device 5054 and comprise suitable circuitry (e.g., discrete logic devices, a processor) to enable communication between the programmable logic device 5054 and the first data circuit. In other forms, the first data circuit interface 5056 may be integral with the logic device 5054.

In certain forms, the first data circuit may store information pertaining to the particular surgical device with which it is associated. Such information may include, for example, a model number, a serial number, a number of operations in which the surgical device has been used, and/or any other type of information. This information may be read by the instrument interface circuit 5050 (e.g., by the logic device 5054), transferred to a component of the non-isolated stage 5002 (e.g., to logic device 5018, DSP processor 5012 and/or UI processor 5014) for presentation to a user via an output device and/or for controlling a function or operation of the generator 5000. Additionally, any type of information may be communicated to first data circuit for storage therein via the first data circuit interface 5056 (e.g., using the logic device 5054). Such information may comprise, for example, an updated number of operations in which the surgical device has been used and/or dates and/or times of its usage.

Additionally, forms of the generator 5000 may enable communication with instrument-based data circuits. For example, the generator 5000 may be configured to communicate with a second data circuit contained in an instrument of a surgical device. The instrument interface circuit 5050 may comprise a second data circuit interface 5058 to enable this communication. In one form, the second data circuit interface 5058 may comprise a tri-state digital interface, although other interfaces also may be used. In certain forms, the second data circuit may generally be any circuit for transmitting and/or receiving data. In one form, for example, the second data circuit may store information pertaining to the particular surgical instrument with which it is associated. Such information may include, for example, a model number, a serial number, a number of operations in which the surgical instrument has been used, and/or any other type of information. In some forms, the second data circuit may store information about the electrical properties of an end effector 30, or attachable components including the electrodes. For example, the first data circuit may indicate a burn-in frequency slope, as described herein. Additionally or alternatively, any type of information may be communicated to second data circuit for storage therein via the second data circuit interface 5058 (e.g., using the logic device 5054). Such information may comprise, for example, an updated number of operations in which the instrument has been used and/or dates and/or times of its usage. In certain forms, the second data circuit may transmit data acquired by one or more sensors (e.g., an instrument-based temperature sensor). In certain forms, the second data circuit may receive data from the generator 5000 and provide an indication to a user (e.g., an LED indication or other visible indication) based on the received data.

In certain forms, the second data circuit and the second data circuit interface 5058 may be configured such that communication between the logic device 5054 and the second data circuit can be effected without the need to provide additional conductors for this purpose (e.g., dedicated conductors of a cable connecting a hand piece to the generator 5000). In one form, for example, information may be communicated to and from the second data circuit using a 1-wire bus communication scheme implemented on existing cabling, such as one of the conductors used transmit interrogation signals from the signal conditioning circuit 5052 to a control circuit in a hand piece. In this way, design changes or modifications to the surgical device that might otherwise be necessary are minimized or reduced. Moreover, because different types of communications implemented over a common physical channel can be frequency-band separated, the presence of a second data circuit may be "invisible" to generators that do not have the requisite data reading functionality, thus enabling backward compatibility of the surgical device instrument.

In certain forms, the isolated stage 5034 may comprise at least one blocking capacitor 5040 connected to the drive signal output 5044 to prevent passage of DC current to a patient. A single blocking capacitor may be required to comply with medical regulations or standards, for example. While failure in single-capacitor designs is relatively uncommon, such failure may nonetheless have negative consequences. In one form, a second blocking capacitor 5042 may be provided in series with the blocking capacitor 5040, with current leakage from a point between the blocking capacitors 5040, 5042 being monitored by, for example, an ADC 5046 for sampling a voltage induced by leakage current. The samples may be received by the logic circuit 5054, for example. Based changes in the leakage current, the generator 5000 may determine when at least one of the blocking capacitors 5040, 5042 has failed. Accordingly, the form of FIG. 50 provides a benefit over single-capacitor designs having a single point of failure.

In certain forms, the non-isolated stage 5002 may comprise a power supply 5006 for outputting DC power at a suitable voltage and current. The power supply may comprise, for example, a 400 W power supply for outputting a 48 VDC system voltage. The power supply 5006 may further comprise one or more DC/DC voltage converters 5060 for receiving the output of the power supply to generate DC outputs at the voltages and currents required by the various components of the generator 5000. As discussed above in connection with the controller 5016, one or more of the DC/DC voltage converters 5060 may receive an input from the controller 5016 when activation of the "on/off" input device by a user is detected by the controller 5016 to enable operation of, or wake, the DC/DC voltage converters 5060.

Figure 51:
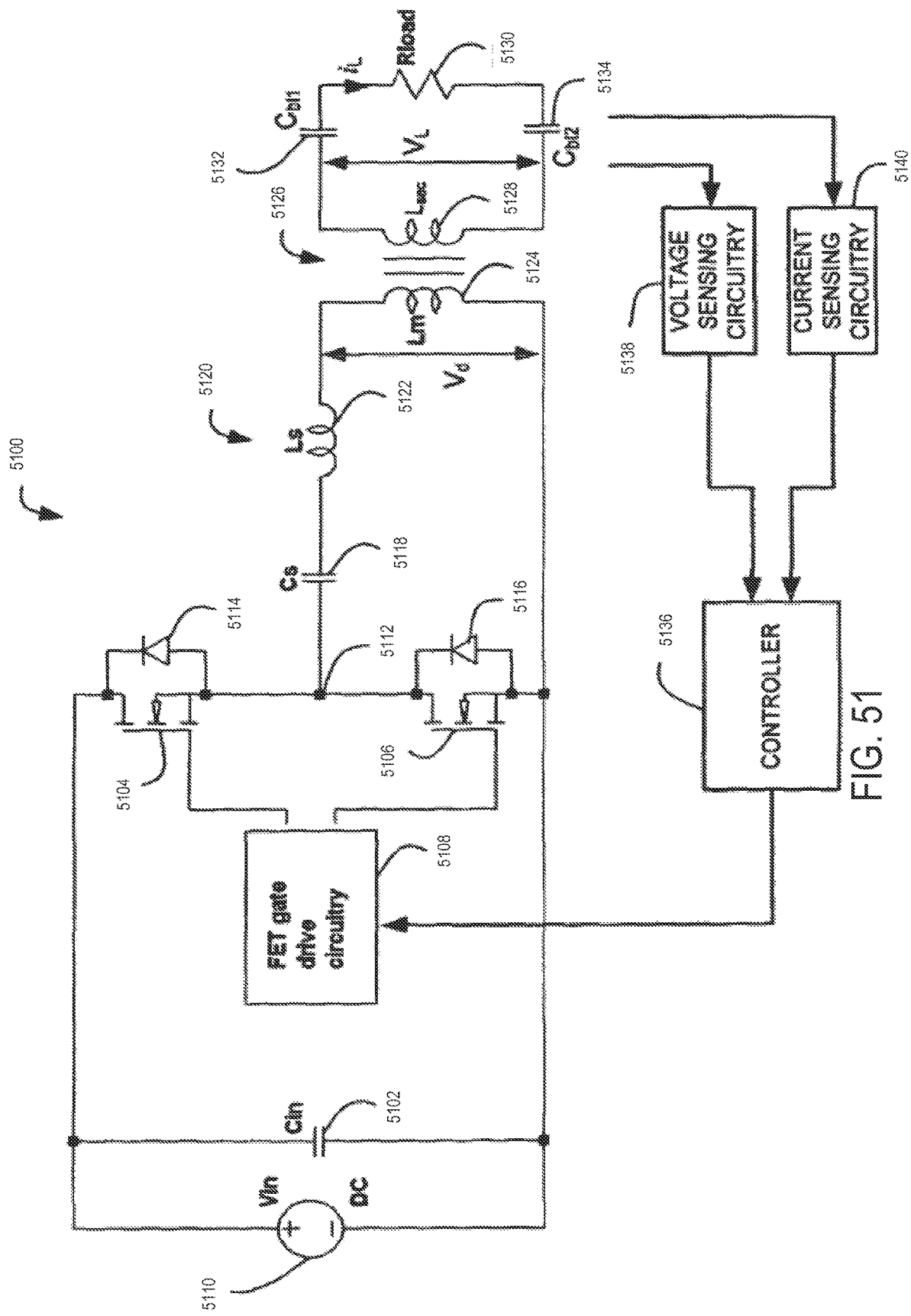
FIG. 51 is a part schematic part block diagram illustrating an RF drive and control circuitry described as one form of the internal generator in FIG. 49 used in some embodiments to generate and control the RF electrical energy supplied to the electrodes in the end effector.

FIG. 51 is a part schematic part block diagram illustrating an RF drive and control circuitry 5100 used in some embodiments to generate and control the RF electrical energy supplied to the electrodes described above. The circuitry 5100 may describe part or all of the components in internal generator 4940 sufficient for providing power and control to the electrodes. As will be explained in more detail below, the drive circuitry 5100 is a resonant based circuit and the control circuitry operates to control the operating frequency of the drive signal so that it is varied around the resonant frequency of the drive circuit, which in turn controls the amount of power supplied to the electrodes at the end effector 30. The way that this is achieved will become apparent from the following description.

As shown in FIG. 51, the drive circuitry 5100 comprises the above described batteries 5110 that are arranged to supply, in this example, 0 and 24V rails. An input capacitor ($C_{in}$) 5102 is connected between the 0V and the 24V rails for providing a low source impedance. A pair of FET switches 5104 and 5106 (both of which are N-channel in this embodiment to reduce power losses) is connected in series between the 0V rail and the 24V rail. FET gate drive circuitry 5108 is provided that generates two drive signals-one for driving each of the two FETs 5104 and 5106. The FET gate drive circuitry 5108 generates drive signals that causes the upper FET (5104) to be on when the lower FET (5106) is off and vice versa. This causes the node 5112 to be alternately connected to the 24V rail (when FET 5104 is switched on) and the 0V rail (when the FET 5106 is switched on). FIG. 51 also shows the internal parasitic diodes 5114 and 5116 of the corresponding FETs 5104 and 5106, which conduct during any periods that the FETs 5104 and 5106 are open.

As shown in FIG. 51, the node 5112 is connected to a capacitor-inductor-inductor resonant circuit 5120 formed by capacitor $C_s$ 5118, inductor $L_s$ 5122 and inductor $L_m$ 5124. The FET gate driving circuitry 5108 is arranged to generate drive signals at a drive frequency ($f_d$) that opens and closes the FET switches 5104 and 5106 at around the resonant frequency of the resonant circuit 5120. As a result of the resonant characteristic of the resonant circuit 5120, the square wave voltage at node 5112 will cause a substantially sinusoidal current at the drive frequency ($f_d$) to flow within the resonant circuit 5120. As illustrated in FIG. 51, the inductor $L_m$ 5124 is the primary of a transformer 5126, the secondary of which is formed by inductor $L_{sec}$ 5128. The transformer 5126 up-converts the drive voltage ($V_d$) across inductor $L_m$ 5124 to the load voltage ($V_L$) that is applied to the load (represented by the load resistance $R_{load}$ 5130 in FIG. 51) corresponding to the impedance of the end effector's jaws and any tissue or vessel gripped by the end effector 30. As shown in FIG. 51, a pair of DC blocking capacitors $C_{bi}$ 5132 and 5134 is provided to prevent any DC signal being applied to the load 5130.

In this embodiment utilizing the internal generator 4940, the amount of electrical power supplied to the end effector 30 is controlled by varying the frequency of the switching signals used to switch the FETs 5104 and 5106. This works because the resonant circuit 5120 acts as a frequency dependent (lossless) attenuator. The closer the drive signal is to the resonant frequency of the resonant circuit 5120, the less the drive signal is attenuated. Similarly, as the frequency of the drive signal is moved away from the resonant frequency of the circuit 5120, the more the drive signal is attenuated and so the power supplied to the load reduces. In this embodiment, the frequency of the switching signals generated by the FET gate drive circuitry 5108 is controlled by a controller 5136 based on a desired power to be delivered to the load 5130 and measurements of the load voltage ($V_L$) and of the load current ($i_L$) obtained by conventional voltage sensing circuitry 5138 and current sensing circuitry 5140. The way that the controller 5136 operates will be described in more detail below.

Figure 52:
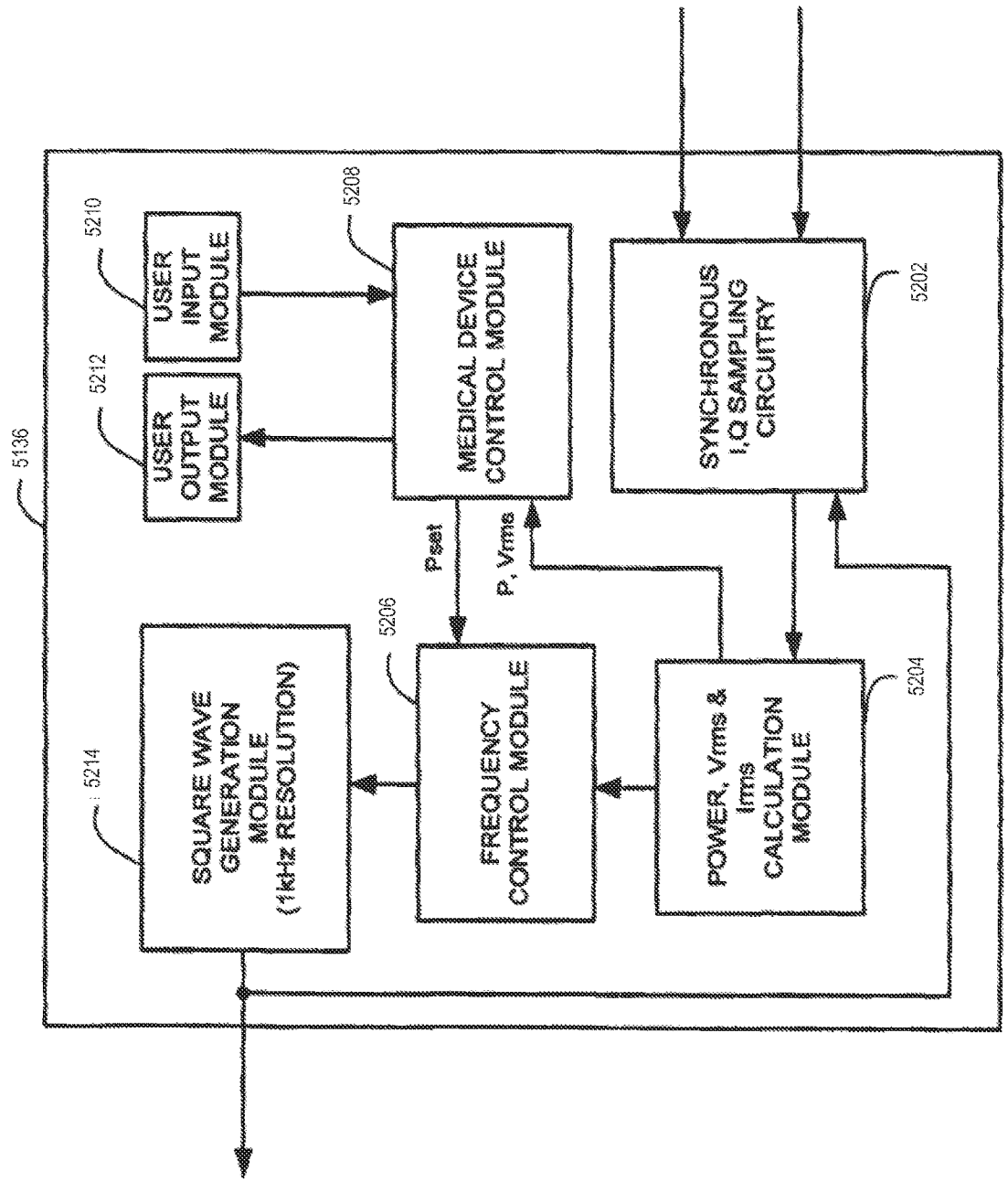
FIG. 52 is a block diagram illustrating the main components of the controller in the internal generator of FIG. 51.

FIG. 52 is a block diagram illustrating the main components of the controller 5136 in the internal generator 4940. In this embodiment, the controller 5136 is a micro-processor based controller and so most of the components illustrated in FIG. 52 are software based components. However, a hardware based controller 5136 may be used instead. As shown, the controller 5136 includes synchronous I,Q sampling circuitry 5202 that receives the sensed voltage and current signals from the sensing circuitry 5138 and 5140 and obtains corresponding samples which are passed to a power, $V_{rms}$ and $I_{rms}$ calculation module 5204. The calculation module 5204 uses the received samples to calculate the RMS voltage and RMS current applied to the load 5130 (end effector 30 and tissue/vessel gripped thereby) and from them the power that is presently being supplied to the load 5130. The determined values are then passed to a frequency control module 5206 and a medical device control module 5208. The medical device control module 5208 uses the values to determine the present impedance of the load 5130 and based on this determined impedance and a pre-defined algorithm, determines what set point power ($P_{set}$) should be applied to the frequency control module 5206. The medical device control module 5208 is in turn controlled by signals received from a user input module 5210 that receives inputs from the user (for example pressing buttons or activating the control levers on the handle 14) and also controls output devices (lights, a display, speaker or the like) on the handle 14 via a user output module 5212.

The frequency control module 5206 uses the values obtained from the calculation module 5204 and the power set point ($P_{set}$) obtained from the medical device control module 5208 and predefined system limits (to be explained below), to determine whether or not to increase or decrease the applied frequency. The result of this decision is then passed to a square wave generation module 5214 which, in this embodiment, increments or decrements the frequency of a square wave signal that it generates by 1 kHz, depending on the received decision. As those skilled in the art will appreciate, in an alternative embodiment, the frequency control module 5206 may determine not only whether to increase or decrease the frequency, but also the amount of frequency change required. In this case, the square wave generation module 5214 would generate the corresponding square wave signal with the desired frequency shift. In this embodiment, the square wave signal generated by the square wave generation module 5214 is output to the FET gate drive circuitry 5108, which amplifies the signal and then applies it to the FET 5104. The FET gate drive circuitry 5108 also inverts the signal applied to the FET 5104 and applies the inverted signal to the FET 5106.

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory, or firmware containing computer program instructions suitable for execution by a general purpose processor or application specific processor. The embodiments, however, are not limited in this context.

The functions of the various functional elements, logical blocks, modules, and circuits elements described in connection with the embodiments disclosed herein may be implemented in the general context of computer executable instructions, such as software, control modules, logic, and/or logic modules executed by the processing unit. Generally, software, control modules, logic, and/or logic modules comprise any software element arranged to perform particular operations. Software, control modules, logic, and/or logic modules can comprise routines, programs, objects, components, data structures, and the like that perform particular tasks or implement particular abstract data types. An implementation of the software, control modules, logic, logic modules, and/or techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, control modules, logic, and/or logic modules may be located in both local and remote computer storage media including memory storage devices.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual embodiments described and illustrated herein has discrete components and features which may be readily separated from or combined with the features of any of the other several aspects without departing from the scope of the present disclosure. Any recited method can be carried out in the order of events recited or in any other order which is logically possible.

Unless specifically stated otherwise, it may be appreciated that terms such as "processing," "computing," "calculating," "determining," or the like, refer to the action and/or processes of a computer or computing system, or similar electronic computing device, such as a general purpose processor, a digital signal processor, application-specific integrated circuit, field programmable gate array, or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers, or other such information storage, transmission, or display devices.

It is worthy to note that some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, and application program interface, exchanging messages, and so forth.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

The invention claimed is:

1. A power and control assembly for controlling a wiping electrode coagulation system of a surgical device comprising a shaft and an end effector coupled distally to the shaft, the power and control assembly comprising:
   a housing structure configured to be attached to the surgical device around the shaft of the surgical device by sliding the housing structure first over the end effector while the end effector is closed and then down a length of the shaft, the housing structure comprising:
   a first wire and a second wire both coupled to a power source
   and entering the housing structure;
   an electrically conductive clamp configured to clamp onto the shaft while the housing structure is attached around the shaft; and
   a substantially conical rotatable nozzle comprising a plurality of indents spacedly distributed around the rotatable nozzle and a plurality of knobs spacedly distributed around the rotatable nozzle and in between each of the plurality of indents, the plurality of knobs configured to cause rotation of the rotatable nozzle as torque is applied to any of the plurality of knobs;
   wherein the first wire is configured to be electrically coupled to the shaft via the electrically conductive clamp;
   wherein the second wire exits the housing structure, and the exiting second wire portion is configured to be electrically coupled to the wiping electrode coagulation system;
   wherein the housing structure is further configured to be detachable from the shaft of the surgical device by sliding the housing structure up the length of the shaft and then over the end effector while the end effector is closed; and wherein the power and control assembly is configured to provide power to the wiping electrode coagulation system.

2. The power and control assembly of claim 1, wherein the housing structure is configured to be rotatable around the shaft as the shaft rotates the end effector.

3. The power and control assembly of claim 1, wherein the rotatable nozzle comprises a plurality of buttons spacedly distributed around the rotatable nozzle and inbetween the plurality of knobs such that a button is always in position to be pressed when approaching the rotatable nozzle substantially from any angle, wherein each of the plurality of buttons is configured to enable power to the wiping electrode coagulation system when activated.

4. The power and control assembly of claim 1, further comprising an external shaft coupled to the housing structure and configured to slidably attach around the shaft of the surgical device.

5. The power and control assembly of claim 1, wherein:
each of the plurality of knobs comprises first and second edges extending radially outward from the rotatable nozzle, and a third edge connecting the first and second edges and extending substantially parallel to a cylindrical curvature of the rotatable nozzle; and
the rotation of the rotatable nozzle caused by the torque occurs when then torque is applied to either of the first or the second edges.

6. The power and control assembly of claim 1, wherein the first and the second wires enter the housing structure at an angle substantially perpendicular to a longitudinal direction of the shaft, according to when the power and control assembly is attached to the surgical device, and the second wire exits the housing structure at an angle substantially parallel to the longitudinal direction of the shaft, according to when the power and control assembly is attached to the surgical device.

7. A surgical device comprising:
a handle assembly;
a shaft coupled to the handle assembly;
an end effector coupled to a distal end of the shaft;
a wiping electrode coagulation system coupled to the end effector and comprising at least one electrode, the wiping electrode coagulation system configured to cause coagulation of tissue through application of electrosurgical energy of the at least one electrode when the at least one electrode is wiped against tissue at a surgical site; and
a power and control assembly comprising:
a housing structure comprising a substantially conical rotatable nozzle comprising a plurality of indents spacedly distributed around the rotatable nozzle and a plurality of knobs spacedly distributed around the rotatable nozzle and in between each of the plurality of indents, the plurality of knobs configured to cause rotation of the rotatable nozzle as torque is applied to any of the plurality of knobs;
the housing structure configured to be attached around the shaft by sliding the housing structure first over the end effector while the end effector is closed and then down a length of the shaft;
a first wire and a second wire coupled to a power source and entering the housing structure; and
an electrically conductive clamp configured to clamp onto the shaft while the housing structure is attached around the shaft;
wherein the first wire is configured to be electrically coupled to the shaft via the electrically conductive clamp;
wherein the second wire exits the housing structure, and the exiting second wire portion is configured to be electrically coupled to the wiping electrode coagulation system;
wherein the housing structure is further configured to be detachable from the shaft by sliding the housing structure up the length of the shaft and then over the end effector while the end effector is closed; and
wherein the power and control assembly is configured to provide power to the wiping electrode coagulation system.

8. The surgical device of claim 7, wherein the wiping electrode coagulation system is configured to be detachable from the end effector.

9. The surgical device of claim 8, wherein the wiping electrode coagulation system further comprises an electrical connector configured to electrically couple to and decouple from the second wire of the power and control assembly.

10. The surgical device of claim 7, wherein the rotatable nozzle comprises a plurality of buttons spacedly distributed around the rotatable nozzle and inbetween the plurality of knobs such that a button is always in position to be pressed when approaching the rotatable nozzle substantially from any angle, wherein each of the plurality of buttons is configured to enable power to the wiping electrode coagulation system when activated.

11. The surgical device of claim 7, wherein:
each of the plurality of knobs comprises first and second edges extending radially outward from the rotatable nozzle, and a third edge connecting the first and second edges and extending substantially parallel to a cylindrical curvature of the rotatable nozzle; and
the rotation of the rotatable nozzle caused by the torque occurs when then torque is applied to either of the first or the second edges.

12. The surgical device of claim 7, wherein the first and the second wires enter the housing structure at an angle substantially perpendicular to a longitudinal direction of the shaft, and the second wire exits the housing structure at an angle substantially parallel to the longitudinal direction of the shaft.

* * * * *